US010125177B2

(12) United States Patent
Zheng et al.

(10) Patent No.: US 10,125,177 B2
(45) Date of Patent: Nov. 13, 2018

(54) TREPONEMA PALLIDUM TRIPLET ANTIGEN

(71) Applicant: Ortho-Clinical Diagnostics, Inc., Raritan, NJ (US)

(72) Inventors: Jian Zheng, Raritan, NJ (US); Renee Yura, Bridgewater, NJ (US); Jianping Yang, Tyler, TX (US)

(73) Assignee: ORTHO-CLINICAL DIAGNOSTICS, INC., Raritan, NJ (US)

( * ) Notice: Subject to any disclaimer, the term of this patent is extended or adjusted under 35 U.S.C. 154(b) by 0 days.

(21) Appl. No.: 15/865,594

(22) Filed: Jan. 9, 2018

(65) Prior Publication Data

US 2018/0141980 A1 May 24, 2018

Related U.S. Application Data

(62) Division of application No. 14/980,200, filed on Dec. 28, 2015, now Pat. No. 9,902,755, which is a division of application No. 14/193,530, filed on Feb. 28, 2014, now Pat. No. 9,221,884, which is a division of application No. 13/350,235, filed on Jan. 13, 2012, now Pat. No. 8,691,950.

(60) Provisional application No. 61/432,570, filed on Jan. 13, 2011.

(51) Int. Cl.
*C07K 14/20* (2006.01)
*G01N 33/571* (2006.01)
*G01N 33/569* (2006.01)

(52) U.S. Cl.
CPC ........ *C07K 14/20* (2013.01); *G01N 33/56911* (2013.01); *G01N 33/571* (2013.01); *C07K 2319/00* (2013.01); *C07K 2319/40* (2013.01); *G01N 2333/20* (2013.01); *G01N 2800/26* (2013.01)

(58) Field of Classification Search
None
See application file for complete search history.

(56) References Cited

U.S. PATENT DOCUMENTS

| 4,514,498 | A  | 4/1985  | Kettman et al. |
| 4,740,467 | A  | 4/1988  | Kettman et al. |
| 4,868,118 | A  | 9/1989  | Norgard |
| 5,330,893 | A  | 7/1994  | Gilbert et al. |
| 5,342,921 | A  | 8/1994  | Cousens et al. |
| 5,350,842 | A  | 9/1994  | Norgard |
| 5,578,456 | A  | 11/1996 | Fujimura et al. |
| 5,681,934 | A  | 10/1997 | Norgard |
| 6,248,331 | B1 | 6/2001  | Ise et al. |
| 6,479,248 | B1 | 11/2002 | Krell et al. |
| 6,794,155 | B2 | 9/2004  | Ise et al. |
| 2001/0002311 | A1 | 5/2001 | Ise et al. |
| 2002/0045278 | A1 | 4/2002 | Saruta et al. |
| 2003/0100103 | A1 | 5/2003 | Saruta et al. |
| 2009/0104650 | A1 | 4/2009 | Walton et al. |

FOREIGN PATENT DOCUMENTS

| EP | 0984065 A1 | 3/2000 |
| WO | WO 2006/138324 A2 | 12/2006 |

OTHER PUBLICATIONS

Akins et al., Lipid Modificiation of the 17-Kilodalton Membrane Immunogen of Treponema pallidum Determines Macrophage Activiation as well Amphiphilicity, Infection and Immunity 61(4):1202-1210 (1993).
Castro et al., Evaluation of an Enzyme Immunoassay Technique for Detection of Antibodies against Treponema pallidum Evaluation of ann enzyme immunoassay technique for, Journal of Clinical Microbiology 41(1): 250-253 (2003).
Hallewell et al., Genetically Engineered Polymers of Human CuZn Superoxide Dismutase, Journal of Biological Chemistry 264(9):5260-5268 (1989).
Morse, Stephen A., Advances in diagnostic tests for bacterial STDs, Salud Publica Mex 45 Supl 5:S698-5708 (2003) English Abstract.
Norgard et al., Cloning and Expression of the Major 47-Kilodalton Surface Immunogen of Treponema pallidum in *Escherichia coli*, Infection and Immunity 54(2):500-506 (1986).
Purcell et al., Molecular Closing and Characterization of the 15-Kilodalton Major immunogen of Treponema pallidum, Infection and Immunity 57(12):3708-3714 (1989).
Schmidt et al., Comparative Evaluation of Nine Different Enzyme-Linked Immunosorbent Assays for Determination of Antibodies against Treponema pallidum in Patients with Primary Syphilis, Journal of Clinical Microbiology 38 (3):1279-1282 (2000).
Chinese Office Action dated Jan. 13, 2016 issued in corresponding Chinese Patent Application No. 201280005276.8, together with an English translation.
Chien, D.Y. et al., "Use of a Novel Hepatitis C Virus (HCV) Major-Epitope Chimeric Polypeptide for Diagnosis of HCV Infection", Journal of Clinical Microbiology, (May 1999), vol. 37, No. 5, pp. 1393-1397.
Hallewell, R.A. et al., "Genetically Engineered Polymers of Human CuZn Superoxide Dismutase", The Journal of Biological Chemistry, (Mar. 25, 1989), vol. 264, No. 9, pp. 5260-5268.
Ismail, N. et al., Laboratory Evaluation of a Fully Automated Chemiluminescence Immunoassay for Rapid Detection of HBsAg, Antibodies to HBsAg, and Antibodies to Hepatitis C Virus, Journal of Clinical Microbiology, (Feb. 2004), vol. 42, No. 2, pp. 610-617.
Richter, S.S., "Laboratory Assays for Diagnosis and Management of Hepatitis C Virus Infection", Journal of Clinical Microbiology, (Dec. 2002), vol. 40, No. 12, pp. 4407-4412.

*Primary Examiner* — Robert A Zeman
(74) *Attorney, Agent, or Firm* — K&L Gates LLP; Louis C. Cullman; Michelle Glasky Bergman

(57) ABSTRACT

A *Treponema pallidum* triplet antigen construct is disclosed which includes three *Treponema pallidum* antigens (TP15, TP17, and TP47), as well as a ten amino acid leader sequence (tag 261) and human copper zinc superoxide dismutase (hSOD). This construct is optimized for in vitro diagnosis of syphilis infection. Plasmids containing DNA encoding the triplet antigen, host cells, production methods, detection methods, and kits are also disclosed.

8 Claims, 9 Drawing Sheets

Figure 1:
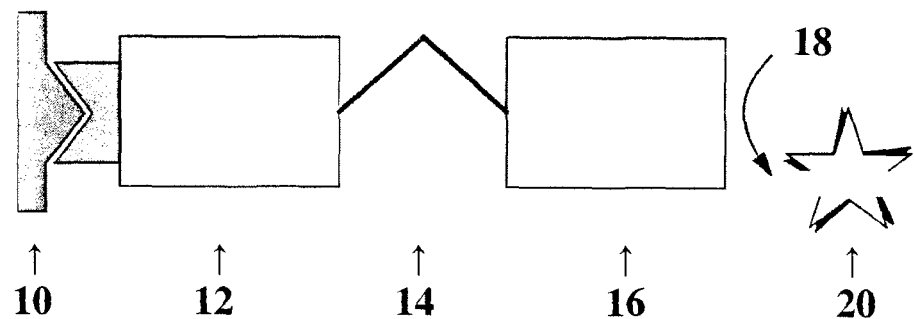
Figure 2:
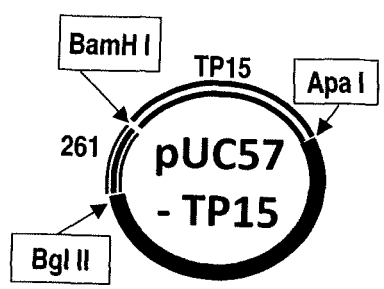
Figure 3:
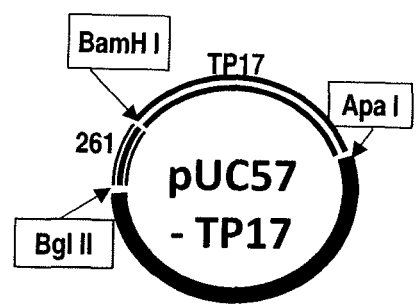
Figure 4:
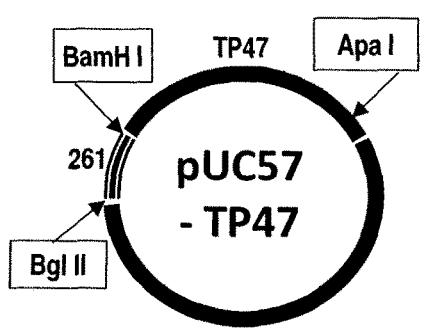
Figure 5:
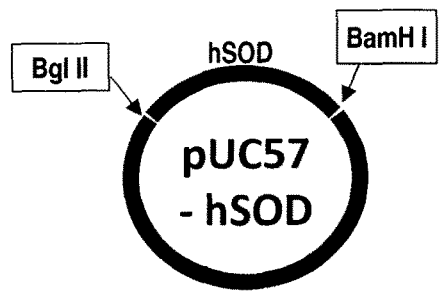

Specification includes a Sequence Listing.

↑     ↑     ↑     ↑     ↑
10   12   14   16   20

TREPONEMA PALLIDUM TRIPLET ANTIGEN

CROSS-REFERENCE TO RELATED APPLICATIONS

This application is a divisional of U.S. application Ser. No. 14/980,200, filed Dec. 28, 2015, now U.S. Pat. No. 9,902,755, which is a divisional of U.S. application Ser. No. 14/193,530, filed Feb. 28, 2014, now U.S. Pat. No. 9,221,884, which is a divisional of U.S. application Ser. No. 13/350,235, filed Jan. 13, 2012, now U.S. Pat. No. 8,691,950, issued Apr. 8, 2014, which claims the benefit of U.S. Provisional Application No. 61/432,570, filed Jan. 13, 2011.

STATEMENT REGARDING FEDERALLY SPONSORED RESEARCH OR DEVELOPMENT

Not applicable.

FIELD OF THE INVENTION

The invention relates to the field of recombinant antigens, and more particularly to a *Treponema pallidum* triplet antigen construct and its use in immunoassays for the detection of syphilis.

BACKGROUND OF THE INVENTION

Over the past half century, effective antibiotic treatment programs have made syphilis relatively uncommon in the United States, with less than 7,100 primary and secondary cases diagnosed in 2003. However, recent data indicates that reported cases are again increasing in subsets of the population, and periodic epidemics of syphilis have occurred for decades. In 1995, the number of new cases of syphilis worldwide was estimated to be 12 million per year. If untreated, syphilis can evolve from localized primary lesions (chancres) to disseminated, chronic infections, including secondary, latent, and tertiary forms.

As a syphilitic infection can produce a variable range of symptoms in humans, laboratory tests are often required to definitively diagnose an infection. Due to the inability to culture the causative organism, *Treponema pallidum* (*T. pallidum*)(TP), in vitro, a need exists for the development and optimization of in vitro methods for the detection of *T. pallidum* in diverse clinical specimens [Morse, Salud Publica Mex 5(Suppl 45):S698-S708, 2003]. While enzyme-linked immunosorbent assays (ELISAs) for *Treponema* are commercially available, they exhibit varying efficiencies at different disease stages [Schmidt et al., J Clin Microbiol 38:1279-1282 (2000)]. Several ELISAs based on whole cell lysate were developed which presented sensitivity of 93.3% to 100% and specificity of 95.5% to 99.8% [Castro et al., J Clin Microbiol 41:250-253 (2003)].

In recent years, several immunodominant and putatively pathogen-specific membrane lipoproteins of *T. pallidum* have been identified in patients with syphilis and in infants with congenital syphilis. These patients and infants developed antigen specific antibodies which could be detected by immunoblot and by enzyme immunoassay. Therefore, recent methods of detection use recombinant antigens, mainly the membrane-integrated proteins 47 kDa, 17 kDa and 15 kDa (TP47, TP17, and TP15, respectively), in treponemal ELISA tests. Although TP47 was the earliest identified, as well as the most abundant and highly immunogenic [Norgard et al., Infect Immun 54:500-506 (1986)], the later identified TP15 and TP17, present in lower amounts, are also strongly immunogenic [Purcell et al., Infect Immun 57:3708-3714 (1989); Akins et al., Infect Immun 61:1202-1210 (1993)].

Given the increase in reported cases of syphilis and the periodic epidemics, as well as the severity of the disease, a need continues to exist for sensitive and specific immunoassays for detection of *Treponema pallidum*.

BRIEF SUMMARY OF THE INVENTION

Figure 17:
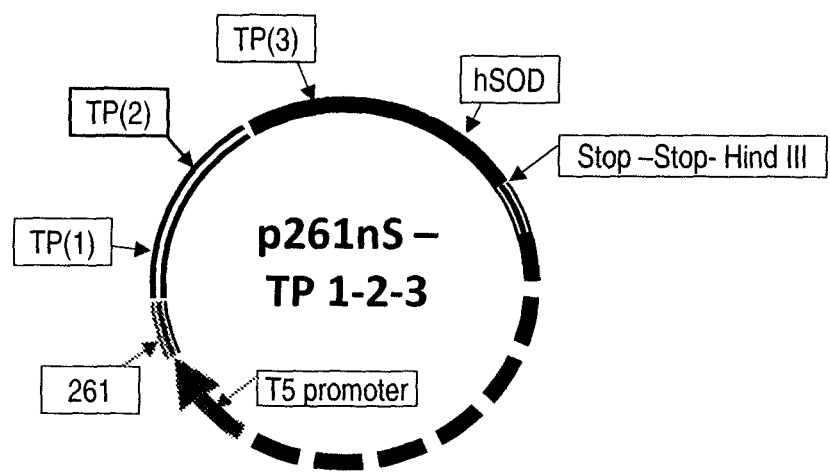
Figure 18:
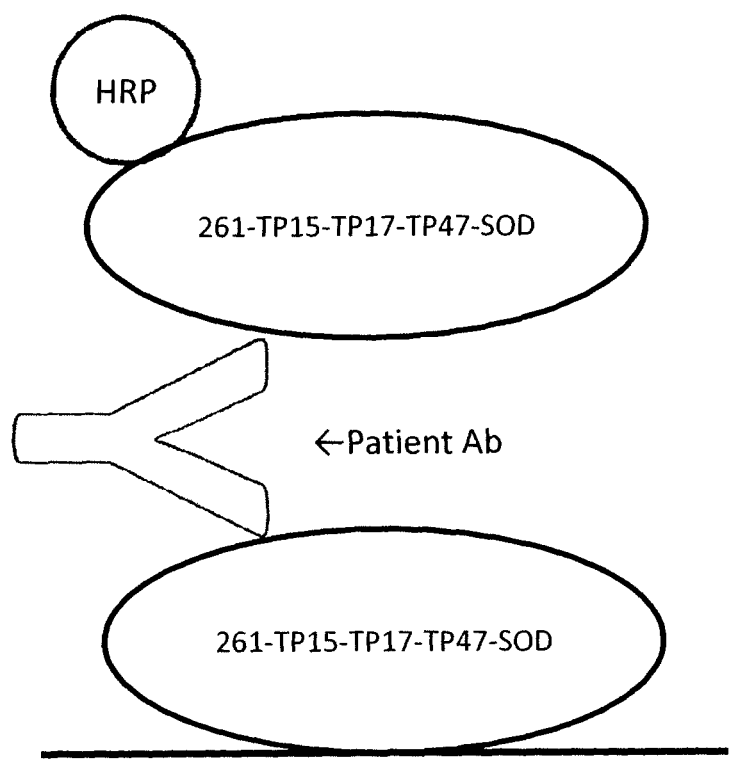
Figure 19:
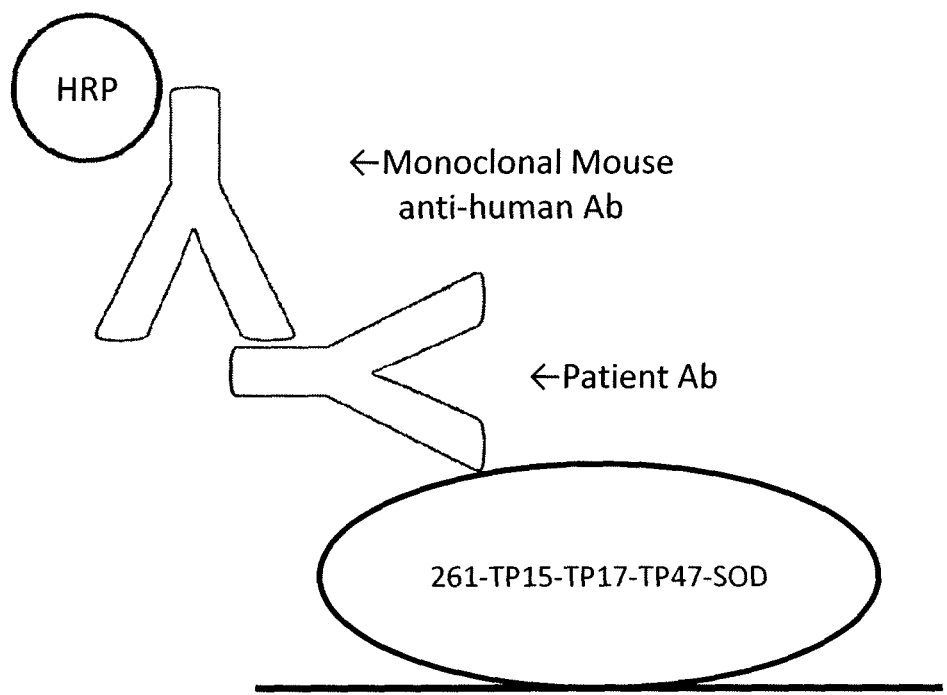

To this end, the invention provides a recombinant plasmid encoding a *Treponema pallidum* triplet antigen. The plasmid comprises nucleic acid encoding an amino acid sequence selected from the group consisting of SEQ ID NO:7, SEQ ID NO:8, SEQ ID NO:9, SEQ ID NO:10, SEQ ID NO:11, and SEQ ID NO:12.

The invention further provides a recombinant plasmid encoding a *Treponema pallidum* triplet antigen, the recombinant plasmid selected from the group consisting of: the plasmid designated p261nS-TP17-15-47 and deposited with the American Type Culture Collection ("ATCC") as ATCC Accession No. PTA-11590 on Jan. 12, 2011; the plasmid designated p261nS-TP47-17-15 and deposited with the American Type Culture Collection as ATCC Accession No. PTA-11589 on Jan. 12, 2011; the plasmid designated p261nS-TP17-47-15; the plasmid designated p261nS-TP47-15-17; the plasmid designated p261nS-TP15-17-47; and the plasmid designated p261nS-TP15-47-17.

Vectors, host cells, and triplet antigen production methods using the host cells are also provided.

Additionally, the invention provides the *Treponema pallidum* triplet antigen having an amino acid sequence selected from the group consisting of SEQ ID NO:7, SEQ ID NO:8, SEQ ID NO:9, SEQ ID NO:10, SEQ ID NO:11, and SEQ ID NO:12. A method of detecting the presence of *Treponema pallidum* antibodies in a sample is further provided, which uses the *Treponema pallidum* triplet antigen, as well as kits for such detection.

Additional features and advantages of the subject invention will be apparent from the description which follows when considered in conjunction with the attached figures.

BRIEF DESCRIPTION OF THE DRAWINGS

FIG. 1 illustrates the reaction scheme for the VITROS® Syphilis TPA test;

FIG. 2 shows the plasmid map of pUC57-TP15;

FIG. 3 shows the plasmid map of pUC57-TP17;

FIG. 4 shows the plasmid map of pUC57-TP47;

FIG. 5 shows the plasmid map of pUC57-hSOD;

FIG. 6 shows the TP construct for cloning into pB10G;

FIG. 7 shows the hSOD construct for cloning into a pB10G triplet plasmid;

FIG. 8 shows the plasmid map of pB10G;

FIG. 9 shows the plasmid map of pB10G-TP(1);

FIG. 10 shows the plasmid map of pB10G-TP(2);

FIG. 11 shows the plasmid map of pB10G-TP(3);

FIG. 12 shows the TP(1) construct for cloning into pB10G-TP(2);

FIG. 13 shows the plasmid map of pB10G-TP(1-2);

FIG. 14 shows the TP(3) construct for cloning into pB10G-TP(1-2);

FIG. 15 shows the plasmid map of pB10G-TP(1-2-3);

FIG. 16 shows the plasmid map of pB10G-TP(1-2-3) with the unique restriction enzyme site;

FIG. 17 shows the plasmid map of p261nS-TP(1-2-3);

FIG. 18 illustrates the direct assay format according to the subject invention; and FIG. 19 illustrates the indirect assay format according to the subject invention.

DETAILED DESCRIPTION OF THE INVENTION

The assay (detection method) of the subject invention uses recombinant *Treponema pallidum* (TP)(the causative agent of Syphilis) outer membrane protein antigens to detect patient sample anti-IgG, anti-IgM, and anti-IgA antibodies. The recombinant protein antigens of interest are a 15 kilodalton antigen (TP15), a 17 kilodalton antigen (TP17), and a 47 kilodalton antigen (TP47). A fused recombinant antigen construct has been developed which incorporates the three antigens of interest as well as human copper zinc superoxide dismutase (hSOD). In addition to the *Treponema pallidum* antigenic sequences and the hSOD, a 10 amino acid tag (the "261sequence") is present at the N-terminus of the fused antigen construct to facilitate evaluation by Western blot and ELISA, and to provide a means for affinity purification if desired. The assay of the subject invention uses this fused recombinant antigen construct.

In one embodiment, the assay is the VITROS® Syphilis TPA test and the assay is performed using the VITROS® ECi/ECiQ Immunodiagnostic Systems, VITROS® 3600 Immunodiagnostic System, or VITROS® 5600 Integrated System using Intellicheck® Technology. Each of these analyzers is available from Ortho-Clinical Diagnostics, Inc. (OCD), 100 Indigo Creek Drive, Rochester, N.Y. 14626. Throughout this application, the use of the trademark VITROS® refers to the line of chemistry and immunodiagnostic analyzers and products commercially available from OCD. The use of the trademark INTELLICHECK® refers to the technology commercially available from OCD which monitors, verifies, and documents diagnostic checks throughout sample and assay processing for accurate and efficient result reporting. An immunometric immunoassay technique is used, which involves the reaction of IgG, IgM or IgA antibodies present in the sample with a biotinylated recombinant TP antigen and a horseradish peroxidase (HRP)-labeled recombinant TP antigen conjugate. The antibody-antigen complex is captured by streptavidin on the wells (SAC wells). Unbound materials are removed by washing. The bound HRP conjugate is measured by a luminescent reaction. A reagent containing luminogenic substrate (a luminol derivative and a peracid salt) and an electron transfer agent is added to the wells. The HRP in the bound conjugate catalyzes the oxidation of the luminol derivative, producing light. The electron transfer agent (a substituted acetanilide) increases the level of light produced and prolongs its emission. The light signals are read by the analyzer system. The bound HRP conjugate is directly proportional to the concentration of anti-TP antibody present. This reaction scheme is illustrated in FIG. 1, where 10 represents the streptavidin coasted well, 12 represents the biotinylated TP antigen, 14 represents the antibodies to TP antigens present in a sample, 16 represents HRP labeled TP antigen, 18 represents signal reagent with enhancer, and 20 represents luminescence. Superoxide dismutase is present in the assay biotin reagent formulation to block binding of anti-SOD antibodies that may be present in the patient sample. This prevents a false reactive signal from being generated.

The invention provides a recombinant plasmid encoding a *Treponema pallidum* triplet antigen. The plasmid comprises nucleic acid encoding an amino acid sequence selected from the group consisting of SEQ ID NO:7, SEQ ID NO:8, SEQ ID NO:9, SEQ ID NO:10, SEQ ID NO:11, and SEQ ID NO:12.

In one embodiment, the plasmid is designated p261nS-TP17-15-47 and is deposited with the American Type Culture Collection ("ATCC") as ATCC Accession No. PTA-11590. Plasmid p261nS-TP17-15-47 includes nucleic acid having the nucleotide sequence as shown in SEQ ID NO:3, encoding the triplet antigen construct having the amino acid sequence as shown in SEQ ID NO:9. In this particular embodiment, amino acids 5-14 encode the 261 tag, amino acids 17-150 encode TP17, amino acids 155-277 encode TP15, amino acids 282-695 encode TP47, and amino acids 697-849 encode hSOD.

In another embodiment, the plasmid is designated p261nS-TP47-17-15 and is deposited with the American Type Culture Collection as ATCC Accession No. PTA-11589. Plasmid p261nS-TP47-17-15 includes nucleic acid having the nucleotide sequence as shown in SEQ ID NO:6, encoding the triplet antigen construct having the amino acid sequence as shown in SEQ ID NO:12. In this particular embodiment, amino acids 5-14 encode the 261 tag, amino acids 17-430 encode TP47, amino acids 435-568 encode TP17, amino acids 573-695 encode TP15, and amino acids 697-849 encode hSOD.

In a further embodiment, the plasmid is designated p261nS-TP17-47-15. Plasmid p261nS-TP17-47-15 includes nucleic acid having the nucleotide sequence as shown in SEQ ID NO:4, encoding the triplet antigen construct having the amino acid sequence as shown in SEQ ID NO:10. In this particular embodiment, amino acids 5-14 encode the 261 tag, amino acids 17-150 encode TP17, amino acids 155-568 encode TP47, amino acids 571-693 encode TP15, and amino acids 695-847 encode hSOD.

In yet another embodiment, the plasmid is designated p261nS-TP47-15-17. Plasmid p261nS-TP47-15-17 includes nucleic acid having the nucleotide sequence as shown in SEQ ID NO:5, encoding the triplet antigen construct having the amino acid sequence as shown in SEQ ID NO:11. In this particular embodiment, amino acids 5-14 encode the 261 tag, amino acids 17-430 encode TP47, amino acids 435-557 encode TP15, amino acids 560-693 encode TP17, and amino acids 695-847 encode hSOD.

In an additional embodiment, the plasmid is designated p261nS-TP15-17-47. Plasmid p261nS-TP15-17-47 includes nucleic acid having the nucleotide sequence as shown in SEQ ID NO:1, encoding the triplet antigen construct having the amino acid sequence as shown in SEQ ID NO:7. In this particular embodiment, amino acids 5-14 encode the 261 tag, amino acids 17-139 encode TP15, amino acids 143-276 encode TP17, amino acids 281-694 encode TP47, and amino acids 696-848 encode hSOD.

In another additional embodiment, the plasmid is designated p261nS-TP15-47-17. Plasmid p261nS-TP15-47-17 includes nucleic acid having the nucleotide sequence as shown in SEQ ID NO:2, encoding the triplet antigen construct having the amino acid sequence as shown in SEQ ID NO:8. In this particular embodiment, amino acids 5-14 encode the 261 tag, amino acids 17-139 encode TP15, amino acids 143-556 encode TP47, amino acids 559-692 encode TP17, and amino acids 694-846 encode hSOD.

The ATCC is located at 10801 University Boulevard, Manassas, Va. 20110-2209 USA, and each of the above deposits was made on Jan. 12, 2011 under the Budapest Treaty on the International Recognition of the Deposit of Microorganisms for the Purposes of Patent Procedure (the "Budapest Treaty").

Each *Treponema pallidum* triplet antigen construct includes three *Treponema pallidum* antigens (TP15, TP17, and TP47). While each has been defined by its amino acid sequence as well as a nucleotide sequence, it should be readily apparent that nucleotide additions, deletions, and/or substitutions, such as those which do not affect the translation of the DNA molecule, are within the scope of a particular nucleotide sequence (i.e. the amino acid sequence encoded thereby remains the same). Such additions, deletions, and/or substitutions can be, for example, the result of point mutations made according to methods known to those skilled in the art. It is also possible to substitute a nucleotide which alters the amino acid sequence encoded thereby, where the amino acid substituted is a conservative substitution or where amino acid homology is conserved. It is also possible to have minor nucleotide additions, deletions, and/or substitutions which do not alter the function of the resulting triplet (i.e. its ability to detect anti-TP15, anti-TP17, and/or anti-TP47 antibodies).

Amino acid additions, deletions, and/or substitutions which do not negate the ability of the resulting triplet to detect anti-TP15, anti-TP17, and/or anti-TP47 antibodies are thus within the scope of a particular amino acid sequence. Such additions, deletions, and/or substitutions can be, for example, the result of point mutations in the DNA encoding the amino acid sequence, such point mutations made according to methods known to those skilled in the art. Substitutions may be conservative substitutions of amino acids. Two amino acid residues are conservative substitutions of one another, for example, where the two residues are of the same type. In this regard, proline, alanine, glycine, serine, and threonine, all of which are neutral, weakly hydrophobic residues, are of the same type. Glutamine, glutamic acid, asparagine, and aspartic acid, all of which are acidic, hydrophilic residues, are of the same type. Another type of residue is the basic, hydrophilic amino acid residue, which includes histidine, lysine, and arginine. Leucine, isoleucine, valine, and methionine, all of which are hydrophobic, aliphatic amino acid residues, form yet another type of residue. Yet another type of residue consists of phenylalanine, tyrosine, and tryptophan, all of which are hydrophobic, aromatic residues. Further descriptions of the concept of conservative substitutions are given by French and Robson [J Molecular Evolution 19:171-175 (1983)], Taylor [J Theor Biol 119: 205-218 (1986)], and Bordo and Argos [J Mol Biol 217: 721-729 (1991)].

While the presently preferred vector system for provision of the nucleic acid encoding the triplet antigen construct is a plasmid vector, other vector systems can also be used. Furthermore, while the presently preferred host cell for expression of the triplet antigen construct is the bacterial host cell *Escherichia coli*, any suitable host and/or vector system can be used to express the triplet antigen construct. Other suitable bacterial hosts, yeasts hosts (such as *Saccharomyces cerevisiae*), as well as mammalian (for example, Hela cells, Cv-1 cells, COS cells) and insect hosts (such as *Drosophila* cell lines), can be used.

Techniques for introducing the nucleic acid molecules into the host cells may involve the use of expression vectors which comprise the nucleic acid molecules. These expression vectors (such as plasmids and viruses; viruses including bacteriophage) can then be used to introduce the nucleic acid molecules into the suitable host cells. For example, DNAencoding the triplet antigen can be injected into the nucleus of a host cell or transformed into the host cell using a suitable vector, or mRNA encoding the triplet antigen can be injected directly into the host cell, in order to obtain expression of triplet antigen in the host cell.

Various methods are known in the art for introducing nucleic acid molecules into host cells. One method is microinjection, in which DNA is injected directly into the nucleus of cells through fine glass needles (or RNA is injected directly into the cytoplasm of cells). Alternatively, DNA can be incubated with an inert carbohydrate polymer (dextran) to which a positively charged chemical group (DEAE, for diethylaminoethyl) has been coupled. The DNA sticks to the DEAE-dextran via its negatively charged phosphate groups. These large DNA-containing particles stick in turn to the surfaces of cells, which are thought to take them in by a process known as endocytosis. Some of the DNA evades destruction in the cytoplasm of the cell and escapes to the nucleus, where it can be transcribed into RNA like any other gene in the cell. In another method, cells efficiently take in DNA in the form of a precipitate with calcium phosphate. In electroporation, cells are placed in a solution containing DNA and subjected to a brief electrical pulse that causes holes to open transiently in their membranes. DNA enters through the holes directly into the cytoplasm, bypassing the endocytotic vesicles through which they pass in the DEAE-dextran and calcium phosphate procedures (passage through these vesicles may sometimes destroy or damage DNA). DNA can also be incorporated into artificial lipid vesicles, liposomes, which fuse with the cell membrane, delivering their contents directly into the cytoplasm. In an even more direct approach, used primarily with plant cells and tissues, DNA is absorbed to the surface of tungsten microprojectiles and fired into cells with a device resembling a shotgun.

Further methods for introducing nucleic acid molecules into cells involve the use of viral vectors. Since viral growth depends on the ability to get the viral genome into cells, viruses have devised clever and efficient methods for doing it. One such virus widely used for protein production is an insect virus, baculovirus. Baculovirus attracted the attention of researchers because during infection, it produces one of its structural proteins (the coat protein) to spectacular levels. If a foreign gene were to be substituted for this viral gene, it too ought to be produced at high level. Baculovirus, like vaccinia, is very large, and therefore foreign genes must be placed in the viral genome by recombination. To express a foreign gene in baculovirus, the gene of interest is cloned in place of the viral coat protein gene in a plasmid carrying a small portion of the viral genome. The recombinant plasmid is cotransfected into insect cells with wild-type baculovirus DNA. At a low frequency, the plasmid and viral DNAs recombine through homologous sequences, resulting in the insertion of the foreign gene into the viral genome. Virus plaques develop, and the plaques containing recombinant virus look different because they lack the coat protein. The plaques with recombinant virus are picked and expanded. This virus stock is then used to infect a fresh culture of insect cells, resulting in high expression of the foreign protein. For a review of baculovirus vectors, see Miller [Bioessays 11:91-95 (1989)]. Various viral vectors have also been used to transform mammalian cells, such as bacteriophage, vaccinia virus, adenovirus, and retrovirus.

As indicated, some of these methods of transforming a cell require the use of an intermediate plasmid vector. U.S. Pat. No. 4,237,224 to Cohen and Boyer describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture. The DNA sequences are cloned into the plasmid vector using standard cloning procedures known in the art, as described by Sambrook et al. [Molecular Cloning: A Laboratory Manual, 2d Edition, Cold Spring Harbor Laboratory Press, Cold Spring Harbor, N.Y. (1989)].

Host cells into which the nucleic acid encoding the triplet antigen has been introduced can be used to produce (i.e. to functionally express) the triplet antigen.

The subject invention further provides a *Treponema pallidum* triplet antigen having an amino acid sequence selected from the group consisting of SEQ ID NO:7, SEQ ID NO:8, SEQ ID NO:9, SEQ ID NO:10, SEQ ID NO:11, and SEQ ID NO:12. Presently preferred embodiments of the triplet antigen are those represented by SEQ ID NO:9 and SEQ ID NO:12. These embodiments present the TP17 portion of the triplet before the TP15 portion of the triplet, and higher antibody detection sensitivity is achieved with these constructs. All constructs include a leader sequence (presently preferred is a ten amino acid leader sequence (tag 261), though other suitable leaders could be substituted). All constructs further include human copper zinc superoxide dismutase (hSOD), a low immunogenic protein, at the carboxy terminus. Eleven lysine residues in the hSOD provide sites for biotin attachment and HRP conjugation, and two cystein residues are mutated to serine (Cys 4 and Cys 112) to prevent interchain protein polymerization [Hallewel et al., J Biol Chem 264:5260-5268 (1989)]. This construct is thus optimized for in vitro diagnosis of syphilis infection. Other suitable low immunogenic proteins which provide similar sites for biotin attachment and HRP conjugation could be substituted. In the presently preferred plasmid construction, the triplet antigen is under the control of the T5 promoter.

While the specific details of an assay for detecting the presence of *Treponema pallidum* antibodies in a sample are disclosed below, generally the method comprises: contacting a sample with the *Treponema pallidum* triplet antigen of the subject invention, wherein *Treponema pallidum* antibodies present in the sample bind to the *Treponema pallidum* triplet antigen forming an antibody/antigen complex; and detecting the antibody/antigen complex, thereby detecting the presence of the *Treponema pallidum* antibodies. For use in an assay format for the detection of antibodies to *Treponema pallidum*, the antigen triplet may be labeled with a detectable marker. Suitable markers include, for example, enzymatic labels such as horseradish peroxidase or alkaline phosphatase, as well as fluorescent labels (such as fluorescein, rhodamine, and green fluorescent protein).

The assay format may also utilize biotin/avidin/streptavidin in the provision of the triplet antigen bound to a solid phase. Suitable solid phases include, for example, any non-aqueous matrix to which the triplet antigen can be bound. Such solid phases are well known in the immunoassay arts, and include, for example, polystyrene plates, polyacrylamides, glass, polysaccharides, polyvinyl alcohol and silicones. Microslides, microwells, and microtips are all used as solid phases in immunoassays.

The assay format may involve direct detection of the antibody/antigen complex (see FIG. 18), which can comprise: contacting the antibody/antigen complex with a second *Treponema pallidum* triplet antigen of the subject invention, wherein the second *Treponema pallidum* triplet antigen is labeled with a detectable marker (HRP as shown). The second *Treponema pallidum* triplet antigen binds to the antibody present in the antibody/antigen complex forming an antigen/antibody/labeled antigen complex, which is then detected thereby detecting the presence of *Treponema pallidum* antibodies in the sample.

The assay format may involve indirect detection of the antibody/antigen complex (see FIG. 19), which can comprise: contacting the antibody/antigen complex with labeled anti-human antibody (monoclonal mouse anti-human antibody as shown). The labeled anti-human antibody binds to the antibody present in the antibody/antigen complex forming an antigen/antibody/labeled anti-antibody complex, which is then detected thereby detecting the presence of *Treponema pallidum* antibodies in the sample.

For all assays of the subject invention, the sample can be any suitable sample (for example, serum, plasma, and EDTA or heparin plasma) but is preferably a serum sample.

The *Treponema pallidum* triplet antigen construct of the subject invention can thus be utilized as a component of a kit for detection of *Treponema pallidum* antibodies. A kit is provided which comprises the *Treponema pallidum* triplet antigen construct, and additionally a second *Treponema pallidum* triplet antigen construct labeled with a detectable marker (an "enzyme conjugate" such as HRP-labeled *Treponema pallidum* triplet antigen)(see above discussion of markers). The kit can also comprise suitable positive and/or negative controls, calibration samples, enzyme conjugates, substrate for enzyme conjugates (such as 0-phenylenediamine), buffer solution, and washing solution.

The details of the construction of the triplet antigen and its use in an assay for detection of *Treponema pallidum* antibodies in a patient sample are described below.

Synthetic Genes. *T. pallidum* outer membrane protein genes TP15, TP17, and TP47 were each synthesized based on amino acid sequence P16055 (amino acid 19-141), P29722 (amino acid 23-156) and P29723 (amino acid 21-434), respectively, published in the central database UniProt (http://www.uniprot.org). Human copper zinc superoxide dismutase (hSOD) gene was synthesized based on amino acid sequence P00441 (amino acid 2-154), except two Cystein residues (amino acid 7 and 112) were mutated to Serine to prevent polymerization. All four synthesized gene codons were optimized for bacterial expression and each was inserted at the EcoR V site on host plasmid pUC57. The resulting plasmids, pUC57-15, pUC57-17, pUC57-45, and pUC57-hSOD, are shown in FIGS. 2-5, respectively.

The four synthetic genes do not bear stop codons and any internal Apa I, BamH I, Bgl II, EcoR I and Hind III sites that were used in subsequent subcloning described below. Restriction enzyme sites, with or without tag gene (261 sequence), were incorporated into the four synthetic genes.

Figure 6:
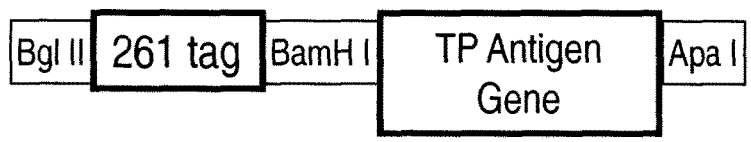
Figure 8:
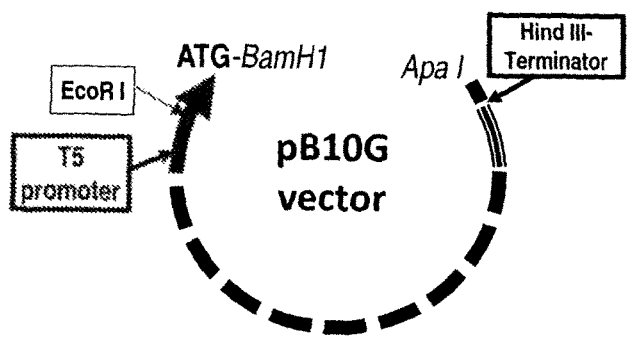
Figure 9:
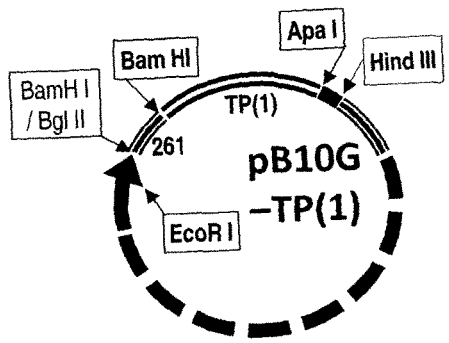
Figure 10:
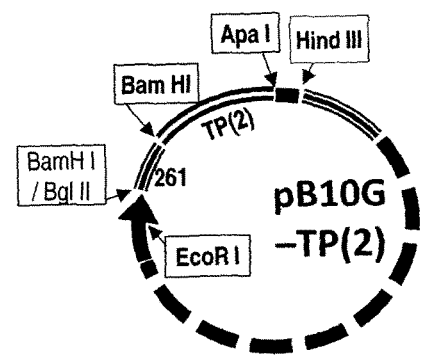
Figure 11:
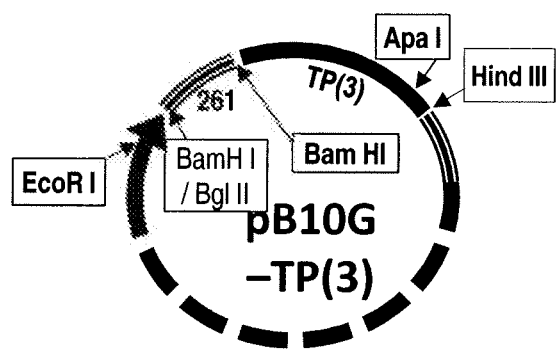
Figure 12:
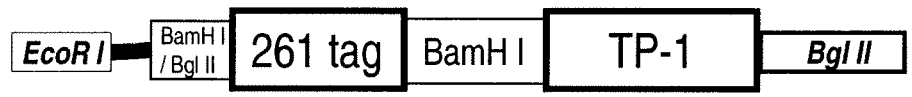
Figure 13:
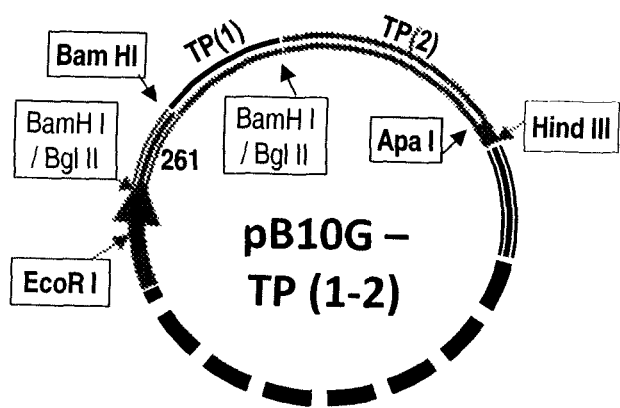

Expression Vector and TP Doublet Construction. Each of the TP genes from pUC57 was digested by Bgl II and Apa I (see FIG. 6 for resulting TP construct) and separately cloned into BamH I and Apa I sites of a previously constructed expression vector, pB10G (see FIG. 8), which contained a T5 promoter, an ATG start site, and unique restriction sites EcoR I, BamH I, Apa I and Hind III. This generated three expressional vectors, pB10G-TP15, pB10G-TP17 and pB10G-TP47 (shown generically as pB10G-TP (1), pB10G-TP(2), and pB10G-TP(3) in FIGS. 9-11, respectively). Ligation of the compatible Bgl II ends of the gene fragments and the BamH I ends on the plasmids eliminated the Bgl II/BamH I restriction enzyme sites in all three constructs. The TP doublet was created by subcloning. To construct a TP doublet subclone (see FIG. 13), a DNA gene insert was produced by PCR reaction using the second antigen expression vector as template and a pair of forward and reverse primers. The forward primer covered the EcoR I site, located in the T5 promoter region, upstream of the TP gene. The reverse primer matched the end of the TP gene and converted the Apa I site to a Bgl II site. This PCR product was then digested with EcoR I/Bgl II (see FIG. 12 for resulting TP-1 construct) and cloned into another antigen expression vector which was cut open with EcoR I and BamH I. Likewise, ligation of the compatible Bgl II on the insert and the BamH I on the host eliminated both restriction enzyme sites.

Figure 14:
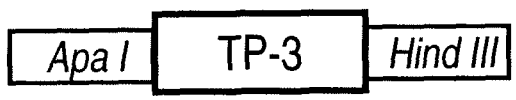
Figure 15:
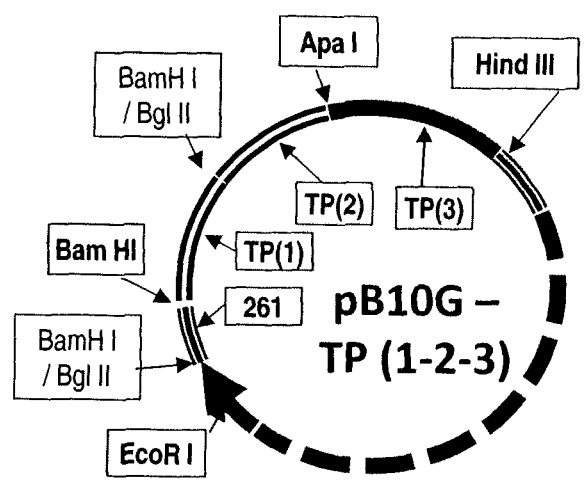

TP Triplet Construction. To produce six final triplet fusion genes, four TP doublet vectors, pB10G-TP17-TP47, pB10G-TP15-TP47, pB10G-TP47-TP15 and pB10G-TP17-TP15, were used as the host and the third TP gene was either added at the 5'end of the TP doublet or added at the 3'end of the TP doublet. The TP(1-2) double vector is shown generically in FIG. 13 and the TP(3) construct for insertion into the doublet vector is shown in FIG. 14. To add the insert at the 3' end, a DNA gene insert was produced by PCR reaction using the third antigen expression vector as template and a pair of forward and reverse primers. The forward primer matched the 5' end of TP gene and contained a Apa I site. The reverse primer matched the 3' end of TP gene and contained a Hind III site. This PCR product was then digested with Apa I/Hind III and cloned into the doublet expression vector which was cut open with the appropriate restriction enzymes. Triplets pB10G-TP15-TP17-TP47, pB10G-TP17-TP15-TP47 and pB10G-TP47-TP17-TP15 were made by adding the third TP gene at the doublet 5'end, while triplets pB10G-TP15-TP47-TP17, pB10G-TP47-TP15-TP17 and pB10G-TP17-TP47-TP15 were made by adding the third TP gene at the doublet 3' end. PCR primers used in creating the doublets and triplets are listed in Table 4, PCR Primers, Group A. This triplet construct is shown generically in FIG. 15.

Figure 7:
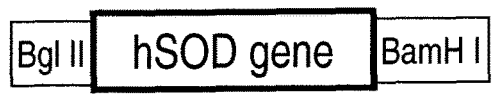
Figure 16:
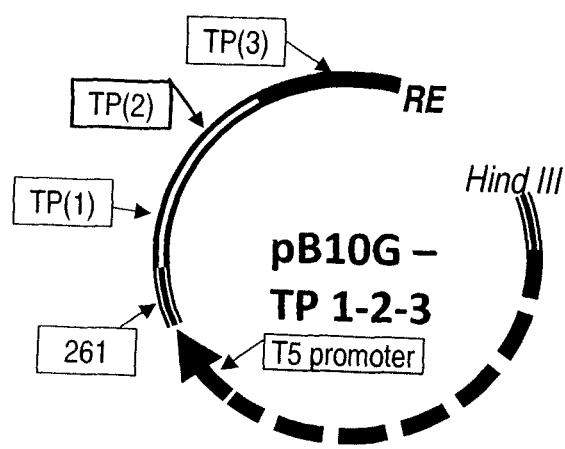

TP Triplet with SOD fusion Construction. The TP triplet with a C-terminal SOD fusion tag (shown generically in FIG. 17) was created through "two-round" PCR and cloning. "Two-round PCR" was performed to link the C-terminal TP3 with SOD (see FIG. 7 for SOD construct) and to introduce restriction enzyme sites for cloning. The first round of PCR was composed of two separate PCR reactions, with the reverse primer (Table 4, PCR Primers, Group B) in one PCR reaction complementing the forward primer (Table 4, PCR Primers, Group C) in the other PCR reaction. In the second round of PCR, the two products from the first round PCR were combined and amplified with a third set of nested primers (Table 4, PCR Primers, Group D). The forward primer matched the TP3 sequence and contained a unique restriction enzyme (RE) site. The reverse primer matched the 3'end SOD. Two stop codons and a Hind III site created a new DNA insert (see FIG. 16). To fuse the SOD gene to the existing *T. pallidum* triplet, the new PCR product was digested and directly cloned into a pB10G-TP triplet plasmid digested at the designed unique restriction site and the Hind III site to yield pB10G-TP(1-2-3)-SOD (see FIG. 17). As used herein, TP1, TP2, and TP3 represent the three *T. pallidum* antigens, TP15, TP17, and TP47, in any order. Thus, TP1 could be TP15, TP2 could be TP17, and TP3 could be TP47. Other combinations include: TP1 could be TP15, TP2 could be TP47, and TP3 could be TP17; TP1 could be TP17, TP2 could be TP15, and TP3 could be TP47; TP1 could be TP17, TP2 could be TP47, and TP3 could be TP15; TP1 could be TP47, TP2 could be TP15, and TP3 could be TP17; and TP1 could be TP47, TP2 could be TP17, and TP3 could be TP15.

All PCR amplifications were performed with Taq polymerase using a standard sequence of 35 PCR cycles: 95° C. (15 sec), 55° C. (20 sec), 72° C. (30 sec). Nucleotide sequences of the PCR primers are listed in Table 4. Usage of each primer in creating particular triplets is indicated. All PCR products were purified following a QIAGEN® PCR kit protocol. All restriction enzymes were purchased from New England Biolabs. Plasmids were prepared using QIAGEN® DNA Miniprep kits. All six triplet coding regions were DNA sequenced (SEQ ID NOs: 1-6) and amino acid sequences translated (SEQ ID NOs:7-12).

The assay of the subject invention provides for the measurement of antibodies to three *T. pallidum* antigens, TP15, TP17 and TP47. The assay is performed on antigen precoated microtiter plates. Samples are added to the microtiter plate wells and incubated. *T. pallidum* IgG/IgM specific antibodies, if present, will bind to and become immobilized by the antigen pre-coated on the wells. The bound antibodies were detected either in a direct conjugated antigen sandwich format (see FIG. 18), or in an indirect format detected by conjugated anti-human IgG and IgM (see FIG. 19).

More particularly, recombinant TP triplets were coated passively on an ELISA high-binding plate well surface as capture antigen. The plate was then blocked with 1% BSA/PBS to cover all unbound well surfaces. Syphilis infected patient's serum or plasma was added in wells and incubated for a first incubation period, enabling *T. pallidum* antibody (IgG, IgM, and IgA) in the sample to react with the pre-coated triplet antigens. Unbound materials were washed away after the first incubation. For the direct assay, HRP conjugated recombinant TP triplet was the detector and was added into the wells and incubated for a second incubation period. After the second incubation, unbound triplet conjugates were washed away. The formed antigen—human *T. pallidum* antibody (IgG/IgM)—antigen complex was measured by adding peroxidase substrate solution, then the reaction was stopped after 30 minutes and optical density was recorded for analysis. For the indirect assay, an HRP conjugated mouse monoclonal anti-human IgG and HRP conjugated mouse monoclonal anti-human IgM mixture was the detector and was added into the wells and incubated for the second incubation period. After the second incubation, unbound conjugates were washed away. The formed anti-human IgG/IgM—human *T. pallidum* antibody (IgG/IgM)—antigen complex was measured by adding peroxidase substrate solution, then the reaction was stopped after 30 minutes and optical density was recorded for analysis.

The engineered recombinant *T. pallidum* triplet has a 10 amino acid leader sequence (tag 261) at the N-terminus and two to four amino acid linkers between each TP antigen. The tag 261 sequence was derived from human placenta growth factor (P1GF). The human copper zinc superoxide dismutase (hSOD) is incorporated at the C-terminus of the *T. pallidum* antigen triplet to form a fusion protein.

hSOD has been used previously in various recombinant antigen fusions in diagnostic assays for infectious pathogens such as HCV, HIV etc. hSOD is a small size, low immunogenic human endogenous protein, which has 153 amino acids with a molecular weight of about 16 kD. The 11 lysine residues in hSOD provide extra conjugation site for biotinylation and HRP conjugation.

Example I

ELISA Assay Reagents, Format, and Protocol

Assay Reagents:
96 well microtiter high-binding plate (COSTAR™)
Coating buffer (10 mM phosphate, 2 mM EDTA, pH 7.0), blocking buffer (1% BSA in PBS, pH 7.0), washing solution (PBS with 0.05% tween-20), sample buffer (Blocker Casein in PBS with 0.05% tween-20, Pierce)
ELISA specimen and conjugate diluent: Blocker Casein in PBS from Pierce. Tween 20 was added to a final of 0.05% before use. In the direct assay, hSOD lysate was added together with HRP conjugated TP triplet.
Purified recombinant TP triplet fusions, their sequences were validated by DNA sequencing (see SEQ ID NOs: 1-6). Proteins were expressed in prokaryotic *E. coli* cells. Protein purity was validated to be greater than 87% by SDS PAGE.
HRP (horseradish peroxidase) conjugated recombinant TP triplet.
150 ng/mL, Phosphate, pH=7.2, Molarity=50 mM
HRP conjugate reagent buffer contains: $H_2O$, $K_2HPO_4$ (anhydrous), $KH_2PO_4$ (anhydrous), NaCl, BSA liquid, KFeCN, ANS, Tween-20, Anti-foam 204, PROCLIN™ 950 (2-methyl-4-isothiazolin-3-one solution)
HRP (horseradish peroxidase) conjugated mouse monoclonal anti-261 tag
HRP (horseradish peroxidase) conjugated mouse monoclonal anti-human IgG
HRP (horseradish peroxidase) conjugated mouse monoclonal anti-human IgM
HRP (horseradish peroxidase) substrate tablet (O-Phenylenediamine-2HCl) and solution and stop solution are components from Ortho-Clinical Diagnostics general ELISA products.
Specimens: Syphilis Positive plasma, Syphilis Negative plasma, SERACARE™ Syphilis mixed titer panel (PS C202) and ZEPTOMETRIX™ Syphilis mixed titer panel (K-ZMC002)

The ELISA Assay Format is shown in FIGS. 18 and 19, both a direct assay format and an indirect assay format.

ELISA Assay Protocol: Plate coating: 1) add 100 uL/well coating solution containing 2 ug/mL of TP triplet fusion at 25° C. for 18 hrs. 2) Wells were washed once with washing buffer and 290 uL/well blocking buffer were added for 1 hr/25° C. blocking. 3) After blocking buffer aspirated, plates were dried greater than 4 hrs in a low humidity incubator. 4) Plate was pouched in an air-proof sealed bag until use.

Direct Assay Protocol: Assay: 1) Add 50 uL Casein (PBS) specimen diluent and 50 uL specimen (or control) to each well. Plate was incubated for 30 min at 37° C. with shaking. 2) After 6 times wash with washing solution; add 100 uL HRP conjugated TP triplet fusion diluted in Casein (PBS) to each well. Plate was incubated for 30 min at 37° C. with shaking. 3) After 6 times wash, add 100 uL OPD substrate and incubate in dark for 30 min at 25° C. 4) Add 25 uL stop solution and read optical density (OD) at 492 nm.

Indirect Assay Protocol: Assay: 1) Add 90 uL Casein (PBS) specimen diluent and 10 uL specimen (or control) to each well. Plate was incubated for 15 min at 37° C. with shaking. 2) After 6 times wash with washing solution; add 100 uL HRP conjugate mixture containing HRP-mouse monoclonal anti-human IgG and HRP-mouse monoclonal anti-human IgM diluted in casein (PBS) to each well. Plate was incubated for 15 min at 37° C. with shaking. 3) After 6 times wash, add 100 uL OPD substrate and incubate in dark for 30 min at 25° C. 4) Add 25 uL stop solution and read optical density (OD) at 492 nm.

Example II

Evaluation of Triplet Constructs

ELISA Reaction: (1) Wells were coated with a serial dilution of six TP triplets and post-coated with 1% BSA in PBS. (2) Add 100 ul HRP conjugated mouse monoclonal anti-261 tag diluted in Casein (PBS) to antigen precoated wells, and incubate at 37° C. for 15 minutes with shaking. (2) Wash 6 times, add 100 uL OPD substrate solution, and incubate at RT for 15 min in dark. (4) Add 25 uL 4N sulfuric acid stop solution and read at 490 nm.

Results shown in Table 1 were ODs. Proposed TP Triplet coating concentrations were derived from calculation to calibrate antigen quantity immobilized on the plate and used in plate coating in the antibody assay evaluation.

ELISA Reaction: (1) Wells were coated with six TP triplets at a concentration defined in Table-1, and post-coated with 1% BSA in PBS. (2) Add 50 ul Casein (PBS) and 50 ul panel specimens to antigen precoated wells, and incubate at 37° C. for 15 minutes with shaking. (3) Wash 6 times, add 100 ul HRP conjugated TP triplet antigens, and incubate at 37° C. for 15 minutes with shaking. HRP conjugated antigen is the antigen coated on the plates. (4) Wash 6 times, add 100 uL OPD substrate solution, and incubate at RT for 15 min in dark. (4) Add 25 uL 4N sulfuric acid stop solution and read at 490 nm.

Results shown in Table 2 were S/C values. S is OD signal, C is cut-off, equals 5 times of an average OD given by three negative controls.

ELISA Reaction: (1) Add 90 ul Casein and 10 ul panel sample (2 fold serial diluted in normal human plasma) to antigen precoated wells, and incubate at 37° C. for 15 minutes with shaking. (2) Wash 6 times, add 100 ul conjugate mixture containing HRP mouse monoclonal anti-human IgG and monoclonal anti-human IgM, and incubate at 37° C. for 15 minutes with shaking. (3) Wash 6 times, add 100 uL OPD substrate solution, and incubate at RT for 15 minutes in dark. (4) Add 25 uL 4N sulfuric acid stop solution and read at 490 nm.

Results shown in Table 3 were final dilution of ZEPTOMETRIX™ panel specimen with normal human plasma (1:X, X=),at which dilution the specimens were determined to be positive (signal over cut-off>1). The cut-off is 5 times of an average OD given by three negative controls.

Example III

Details of VITROS® Syphilis TPA Test

The principles of the VITROS® Syphilis TPA test using the TP15-TP17-TP47 triplet construct are as described above and as shown in FIG. 1. A kit is provided which includes a reagent pack and a calibrator. The reagent pack contains: 100 coated wells (streptavidin, bacterial; binds ≥2 ng biotin/well); 13.1 mL biotinylated antigen reagent (biotin-recombinant TP antigens 0.15 ug/mL) in buffer with bovine gamma globulin, bovine serum albumin, and antimicrobial agent; and 20.4 mL conjugate reagent (HRP-recombinant TP antigens, 0.15 ug/mL) in buffer with bovine serum albumin and antimicrobial agent). The calibrator contains VITROS® Syphilis TPA Calibrator (human syphilis IgG positive plasma, 2.2 mL) with antimicrobial agent. The test uses 25 uL of calibrator for each determination.

Suitable specimens for use with the test are serum, heparin plasma, EDTA plasma, and citrate plasma. The test uses 25 uL of sample (specimen) for each determination.

The test also uses signal reagent (such as VITROS® Immunodiagnostic Products Signal Reagent), wash reagent (such as VITROS® Immunodiagnostic Products Universal Wash Reagent), and quality control materials (such as VITROS® Immunodiagnostic Products Syphilis TPA Controls).

The test uses a 16-minute first incubation period, and an 8-minute second incubation period, with a time for first result of 34 minutes. The test is performed at 37° C.

Results are automatically calculated by the VITROS® Immunodiagnostic and VITROS® Integrated Systems, and represent "signal for test sample"/"signal at cutoff (cutoff value)". Samples with results of <0.80 will be flagged as "negative", samples with results ≥0.80 and <1.20 will be flagged as "borderline", and samples with results ≥1.20 will be flagged as "reactive". Negative indicates no active or previous infection with *Treponema pallidum*; borderline indicates the test is unable to determine if *Treponema pallidum* infection has occurred, and the sample should be re-tested; and reactive indicates active or previous infection with *Treponema pallidum*.

Example IV

Performance Characteristics of the VITROS® Syphilis TPA Test

Referring to Table 5, initial sensitivity and specificity was assessed on a population of 4290 samples using the VITROS® Syphilis TPA test and a commercially available immunoassay ("IA 1") for antibodies to *Treponema pallidum*. An initial analysis in the VITROS® Syphilis TPA test gave an initial specificity, including borderline samples (4015/4016) of 99.98% (exact 95% Cl 99.9-100.0%). Initial sensitivity, including borderline samples (266/274) was 97.08% (exact 95% Cl 94.3-98.7%). One (0.025%) sample was borderline in the VITROS® Syphilis TPA test. The commercially available test did not have a borderline region.

Referring to Table 6, relative specificity and sensitivity after resolution of uninterpretable samples was assessed. This included samples where there was a difference in classification from the commercial test (reactive/negative) (defined as "discordant"). Samples that resulted in discordant or borderline results (either in the VITROS® or IA 1 test) were further tested to determine relative sensitivity and specificity. A total of 9 discordant and borderline samples were further tested by first repeating the VITROS® Syphilis TPA test in duplicate. A total of 9 discordant and borderline samples remained discordant with IA 1 after repeat testing in the VITROS® Syphilis TPA test. The 9 samples were also tested in up to 4 additional commercially available assays for antibodies to *Treponema pallidum*. The median VITROS® Syphilis TPA result was then compared to the consensus classification of the other 4 commercially available tests. Using this algorithm, 8 samples were resolved as syphilis antibody negative and one sample remained borderline in the VITROS® Syphilis TPA test. After resolution of discordant results, the relative specificity of the VITROS® Syphilis TPA test to the IA 1 test was calculated (4023/4024) as 99.98% (exact Cl 99.9-100.0%) and relative sensitivity (266/266) as 100% (exact Cl 98.6-100.0%).

Referring to Table 7, 149 samples containing potentially cross-reacting sub-groups were tested in the VITROS® Syphilis TPA test and in a commercially available test (EIA 1). The sub-groups included: HAV IgG and IgM, HBV IgG and IgM, HCV IgG and IgM, EBV IgG and IgM, anti-HSV IgG and IgM, anti-HIV 1/2 IgG and IgM, CMV IgG and IgM, Rubella IgG and IgM, ANA/SLE, *Borrelia burgdorferi* infection (European and US strain), *Toxoplasma gondii* infections IgG and IgM, heterophilic antibodies/HAMA and Rheumatoid factor. The specificity (137/137) was 100.0% (95% Cl 97.3-100.0%) and sensitivity (12/12) was 100.0% (95% Cl 73.5%-100.0%). No discordant samples were observed and all results were in line with the expected clinical performance in the commercially available test. Thus, none of the samples was found to cross react with the VITROS® Syphilis TPA assay to cause any mis-classification of results.

Precision on the VITROS® ECi/ECiQ Immunodiagnostic System was evaluated. Two replicates each of 4 patient sample pools and 4 control samples were tested on 2 separate occasions per day on at least 20 different days. The experiment was performed using 2 reagent lots on two different systems. Precision on the VITROS® 3600 Immunodiagnostic System and the VITROS® 5600 Integrated System was also evaluated. Two replicates each of 4 patient sample pools and 4 control samples were tested on 2 separate occasions per day on at least 20 different days. The experiment was performed using 1 reagent lot on each system. Results showed precision for samples at the cut off up to strong positives averaged 1.6% (range 0.9-3.2%) within run, 4.8% (range 2.7-9.0%) within calibration, and 4.6% (range 2.1-9.0%) within lab. The VITROS® Syphilis TPA test thus gives excellent precision across the borderline and reactive ranges, on all VITROS® systems.

Referring to Table 8, the VITROS® Syphilis TPA test was evaluated for interference. Of the compounds tested, none was found to interference with the clinical interpretation of the test at the concentration indicated.

The VITROS® Syphilis TPA test was also evaluated with two sets of proficiency samples from CAP and NEQAS and two commercially available performance panels (ZEPTOMETRIX™ and BBI-SERACARE™). 100% agreement was obtained with these proficiency samples and performance panels.

Samples types were also evaluation on the VITROS® Syphilis TPA test. Five normal donor samples were collected as serum (SST, clot activator and on the clot glass tubes), as heparin plasma (lithium and sodium), EDTA plasma and citrate plasma. From five other donors, 50 mL of whole blood was collected. This was spiked with a syphilis reactive plasma and dispensed into the same type of tubes as mentioned above to mimic syphilis reactive donors. Bias between sample type was assessed. No large differences were observed between sample types compared to serum. For citrate samples, the recovery compared to serum was lower due to the dilutional effect of the citrate. A stability study using these samples demonstrated that samples can be stored for 7 days at 2-8° C. and 4 weeks at −20° C. without significant loss of dose results or change in clinical classification.

Taking all performance characteristics into account, the VITROS® Syphilis TPA test combines good analytical and clinical performance with the operational simplicity of a rapid automated continuous random access immunoassay.

While particular embodiments of the invention have been shown, it will be understood, of course, that the invention is not limited thereto, since modifications may be made by those skilled in the art, particularly in light of the foregoing teachings. Reasonable variation and modification are possible within the scope of the foregoing disclosure of the invention without departing from the spirit of the invention.

TABLE 1

Calibration Coated Six TP Triplet Antigens on Plate

| Plate coated TP | OD signal probed by HRP anti-261 (2 ng/mL) | | | | | | Proposed TP Triplet coating |
|---|---|---|---|---|---|---|---|
| Triplet [ug/ml] | 4.00 | 2.00 | 1.00 | 0.50 | 0.25 | 0.13 | [ug/mL] |
| TP15-17-47-SOD | over | 3.006 | 2.372 | 1.490 | 0.914 | 0.613 | 1.00 |
| TP15-47-17-SOD | over | 2.916 | 2.106 | 1.356 | 0.843 | 0.566 | 1.20 |
| TP17-15-47-SOD | over | 3.144 | 3.193 | 2.508 | 1.494 | 0.891 | 0.50 |
| TP17-47-15-SOD | over | 1.454 | 0.914 | 0.580 | 0.346 | 0.263 | 2.80 |
| TP47-15-17-SOD | over | 3.310 | 2.481 | 1.950 | 1.209 | 0.713 | 0.65 |
| TP47-17-15-SOD | over | 3.523 | 3.626 | 3.489 | 2.434 | 1.426 | 0.25 |

TABLE 2

Evaluation of Syphilis Reactive Specimens by Direct ELISA

Plate: TP Triplet Coated

SeraCare Syphilis mixed titer panel (PS C202)-(S/C Values)

| ID | [ug/ml] | #1 | #2 | #3 | #4 | #5 | #6 | #7 | #8 | #9 | #10 |
|---|---|---|---|---|---|---|---|---|---|---|---|
| TP15-17-47-SOD | 1.00 | 3.0 | 5.4 | 1.1 | 0.0 | 2.6 | 2.6 | 8.0 | 1.3 | 7.7 | 4.0 |
| TP15-47-17-SOD | 1.20 | 4.5 | 7.2 | 2.7 | 0.0 | 1.8 | 4.5 | 14 | 4.0 | 7.8 | 6.1 |
| TP17-15-47-SOD | 0.50 | 4.9 | 10 | 3.4 | 0.0 | 3.0 | 4.9 | 15 | 6.7 | 15 | 6.7 |
| TP17-47-15-SOD | 2.80 | 3.1 | 8.8 | 3.0 | 0.0 | 2.6 | 4.9 | 4.7 | 5.6 | 15 | 6.7 |
| TP47-15-17-SOD | 0.65 | 4.4 | 9.7 | 1.9 | 0.0 | 3.1 | 4.9 | 17 | 3.4 | 15 | 5.4 |
| TP47-17-15-SOD | 0.25 | 4.9 | 10 | 3.3 | 0.0 | 4.2 | 4.9 | 15 | 6.0 | 15 | 6.7 |

Plate: TP Triplet Coated

| ID | [ug/ml] | #11 | #12 | #13 | #14 | #15 | #16 | #17 | #18 | #19 | #20 |
|---|---|---|---|---|---|---|---|---|---|---|---|
| TP15-17-47-SOD | 1.00 | 2.1 | 3.3 | 3.2 | 2.9 | 5.3 | 0.0 | 3.1 | 2.6 | 2.8 | 3.9 |
| TP15-47-17-SOD | 1.20 | 3.0 | 6.1 | 6.9 | 8.1 | 6.9 | 0.0 | 3.2 | 7.0 | 4.0 | 2.8 |
| TP17-15-47-SOD | 0.50 | 6.3 | 6.7 | 11 | 7.5 | 10 | 0.0 | 4.6 | 16 | 4.5 | 10 |
| TP17-47-15-SOD | 2.80 | 5.6 | 4.0 | 14 | 6.2 | 10 | 0.0 | 3.6 | 10 | 4.2 | 5.3 |
| TP47-15-17-SOD | 0.65 | 4.9 | 6.1 | 11 | 6.6 | 10 | 0.0 | 2.5 | 5.0 | 5.8 | 5.6 |
| TP47-17-15-SOD | 0.25 | 7.0 | 6.7 | 11 | 9.7 | 13 | 0.0 | 3.5 | 12 | 3.9 | 9.0 |

TABLE 3

Evaluation of Plate Coating Antigen Sequence Combination

Plate: TP Triplet Coated

ZeptoMetrix Mixed Titer Syphilis Panel (K-ZMC002)

| ID | [ug/ml] | #1 | #2 | #3 | #4 | #5 | #6 | #7 | #8 |
|---|---|---|---|---|---|---|---|---|---|
| TP15-17-47-SOD | 1.00 | 2 | 2 | 2 | 4 | 8 | 8 | 8 | 2 |
| TP15-47-17-SOD | 1.20 | 4 | 2 | 2 | 8 | 4 | 16 | 8 | 2 |
| TP17-15-47-SOD | 0.50 | 16 | 4 | 2 | 256 | 32 | 64 | 256 | 8 |
| TP17-47-15-SOD | 2.80 | 8 | 2 | 2 | 32 | 4 | 8 | 64 | 2 |
| TP47-15-17-SOD | 0.65 | 16 | 2 | 4 | 64 | 32 | 16 | 256 | 8 |
| TP47-17-15-SOD | 0.25 | 32 | 4 | 4 | 256 | 16 | 64 | 256 | 8 |

Plate: TP Triplet Coated

| ID | [ug/ml] | #9 | #10 | #11 | #12 | #13 | #14 | #15 |
|---|---|---|---|---|---|---|---|---|
| TP15-17-47-SOD | 1.00 | 2 | 32 | 2 | 2 | 4 | 256 | 8 |
| TP15-47-17-SOD | 1.20 | 2 | 16 | 2 | 2 | 4 | 32 | 8 |
| TP17-15-47-SOD | 0.50 | 32 | 256 | 8 | 64 | 32 | 256 | 32 |
| TP17-47-15-SOD | 2.80 | 2 | 256 | 2 | 8 | 8 | 256 | 16 |
| TP47-15-17-SOD | 0.65 | 16 | 256 | 4 | 16 | 16 | 256 | 32 |
| TP47-17-15-SOD | 0.25 | 16 | 256 | 8 | 32 | 16 | 256 | 64 |

TABLE 4

PCR Primers

| Group | Name | Primer Direction | Primers used in creating triplet of ||||||  Comments |
|---|---|---|---|---|---|---|---|---|---|
| | | | 15-17-47 | 17-15-47 | 15-47-17 | 47-15-17 | 17-47-15 | 47-17-15 | |
| A | F4-ER | Forward | yes | yes | yes | yes | yes | yes | EcoR I, vector sequence |
| | Apa-TP15 | Forward | | | | | yes | | Apa -(TP15)... |
| | Apa-TP17 | Forward | | | yes | yes | | | Apa -(TP17)... |
| | TP15-BG | Reverse | | yes | | | | | ...TP15-gly-pro-Bgl II |
| | TP15-BG2 | Reverse | yes | | yes | | | | ...TP15-gly-Bgl II |
| | TP17-BG | Reverse | yes | yes | | | yes | yes | ...TP17-gly-pro-Bgl II |
| | TP47-BG2 | Reverse | | | | yes | | yes | ...TP47-gly-pro-Bgl II |
| B | F-15 | Forward | | | | | yes | yes | 50 bp before SacI in TP15 |
| | R-15S | Reverse | | | | | yes | yes | TP15(3')-SOD(5') |
| | T17-BH | Forward | | | yes | yes | | | 95 bp before Eag I in TP17 |
| | R-17S | Reverse | | | yes | yes | | | TP17(3')-SOD(5') |
| | F-47b | Forward | yes | yes | | | | | 50 bp before Xma in TP47 |
| | R-47S | Reverse | yes | yes | | | | | TP47(3')-SOD(5') |
| C | F-15S | Forward | | | | | yes | yes | TP15(3')-SOD(5') |
| | F-17S | Forward | | | yes | yes | | | TP17(3')-SOD(5') |
| | F-47S | Forward | yes | yes | | | | | TP47(3')-SOD(5') |
| | RS | Reverse | yes | yes | yes | yes | yes | yes | downstream of SOD gene |
| D | T15-Sac | Forward | | | | | yes | yes | (TP15)...SacI... |
| | TP17-EAG | Forward | | | yes | yes | | | (TP17)...EagI... |
| | T47-XMA | Forward | yes | yes | | | | | (TP47)...XmaI... |
| | RS-H3 | Reverse | yes | yes | yes | yes | yes | yes | SOD(3')-StopStop-Hind III |

| Group | Name | Primer Sequence (5'-3') |
|---|---|---|
| A | F4-ER | SEQ ID NO: 13: cacaGAATTCATTAAAGAGGAGAAATTAAC |
| | Apa-TP15 | SEQ ID NO: 14: tgtctGGGCCCAGCTTTTCTAGTATTCCGA |
| | Apa-TP17 | SEQ ID NO: 15: tgtctGGGCCCGTGAGCTGCACCACGGT |
| | TP15-BG | SEQ ID NO: 16: agctggAGATCTCGGGCCGCGAGAGATAATGGCTTCTT |
| | TP15-BG2 | SEQ ID NO: 17: gctggAGATCTACCGCGAGAGATAATGGCTTCTT |
| | TP17-BG | SEQ ID NO: 18: agctggAGATCTCGGGCCTTTCTTGGTTTTCTTCAGAACGTA |
| | TP47-BG2 | SEQ ID NO: 19: agctggAGATCTTGGACCCTGCGCCACCACTTTCGCG |
| B | F-15 | SEQ ID NO: 20: CGCGACCGTGAGCTCTCAGAGTTTT |
| | R-15S | SEQ ID NO: 21: CAGCACGCTGACGGCTTTGGTCGCgagGCGAGAGATAATGGCTTCTTTTTCGCC |
| | T17-BH | SEQ ID NO: 22: GTGAGCTGCACCACGGT |
| | R-17S | SEQ ID NO: 23: CAGCACGCTGACGGCTTTGGTCGCgagTTTCTTGGTTTTCTTCAGAACGTAAA |
| | F-47b | SEQ ID NO: 24: GGTTAGCGATCAGGCCGT |
| | R-47S | SEQ ID NO: 25: CAGCACGCTGACGGCTTTGGTCGCgagCTGCGCCACCACTTTCGCGCGC |
| C | F-15S | SEQ ID NO: 26: GGCGAAAAAGAAGCCATTATCTCTCGCctcGCGACCAAAGCCGTCAGCGTGCTG |
| | F-17S | SEQ ID NO: 27: TTTACGTTCTGAAGAAAACCAAGAAActcGCGACCAAAGCCGTCAGCGTGCTG |
| | F-47S | SEQ ID NO: 28: GCGCGCGAAAGTGGTGGCGCAGctcGCGACCAAAGCCGTCAGCGTGCTG |
| | RS | SEQ ID NO: 29: TGCAGTCGACGGGCCCGGGAT |
| D | T15-Sac | SEQ ID NO: 30: CGCGACCGTGAGCTCTCAGAGTTTT |
| | TP17-EAG | SEQ ID NO: 31: CCCTGCCGGCCGCAGATTGT |
| | T47-XMA | SEQ ID NO: 32: GGATTTCACCCCGGGTACCGAATATA |
| | RS-H3 | SEQ ID NO: 33: agccAAGCTTcattaCTGGGCGATACCAATAACGCCA |

TABLE 5

| | | VITROS Syphilis TPA Test | | | |
|---|---|---|---|---|---|
| | | Reactive | Borderline | Negative | Total |
| IA 1 | Reactive | 266 | 0 | 8 | 274 |
| | Negative | 0 | 1 | 4015 | 4016 |
| | Totals | 266 | 1 | 4023 | 4290 |

TABLE 6

| | | VITROS Syphilis TPA Test | | | |
|---|---|---|---|---|---|
| | | Reactive | Borderline | Negative | Total |
| IA 1 | Reactive | 266 | 0 | 0 | 266 |
| | Negative | 0 | 1 | 4023 | 4024 |
| | Totals | 266 | 1 | 4023 | 4290 |

TABLE 7

| | | VITROS Syphilis TPA Test | | | |
|---|---|---|---|---|---|
| | | Reactive | Borderline | Negative | Total |
| EIA 1 | Reactive | 12 | 0 | 0 | 12 |
| | Negative | 0 | 0 | 137 | 137 |
| | Totals | 12 | 0 | 137 | 149 |

TABLE 8

| Compound | Concentration | |
|---|---|---|
| Azide (sodium) | 20 mg/dL | 3.06 mmol/L |
| Bilirubin | 20 mg/dL | 0.342 mmol/L |
| Biotin | 1000 ng/dL | 40.8 nmol/L |
| BSA (High Protein) | 5 g/dL (total ~12 g/dL) | N/A |
| Cholesterol | 250 mg/dL | N/A |
| Hemoglobin (hemolysate) | 500 mg/dL | 0.155 mmol/L |
| Intralipid | 850 mg/dL | N/A |
| Triolein | 3000 mg/dL | 33.96 mmol/L |

The invention claimed is:

1. A *Treponema pallidum* triplet antigen comprising the amino acid sequence as shown in SEQ ID NO:10.

2. The *Treponema pallidum* triplet antigen of claim 1 labeled with a detectable marker.

3. The *Treponema pallidum* triplet antigen of claim 2 wherein the detectable marker is horseradish peroxidase.

4. A kit for detection of *Treponema pallidum* antibodies, the kit comprising:
   the *Treponema pallidum* triplet antigen of claim 1; and
   a second *Treponema pallidum* triplet antigen of claim 1, the second *Treponema pallidum* triplet antigen labeled with a detectable marker.

5. The kit of claim 4 further comprising positive or negative controls.

6. The kit of claim 4 further comprising calibration samples.

7. The kit of claim 4 further comprising one or more of enzyme conjugate, substrate for enzyme conjugate, buffer solution, and washing solution.

8. A method of detecting the presence of *Treponema pallidum* antibodies in a sample, the method comprising:
   contacting the sample with a first antigen which is immobilized on a solid support and which comprises the *Treponema pallidum* triplet antigen of claim 1, wherein *Treponema pallidum* antibodies present in the sample bind to the *Treponema pallidum* triplet antigen forming an antibody/antigen complex; and
   detecting the antibody/antigen complex, thereby detecting the presence of *Treponema pallidum* antibodies.

\* \* \* \* \*

SEQUENCE LISTING

<160> NUMBER OF SEQ ID NOS: 33

<210> SEQ ID NO 1
<211> LENGTH: 2544
<212> TYPE: DNA
<213> ORGANISM: Treponema pallidum

<400> SEQUENCE: 1

```
atgcgtggat ctgctgtgcc gcctcaacag tgggccttgt ctggatccag cttttctagt      60
attccgaacg gcacctatcg tgcgacgtac caggatttcg atgaaaatgg ttggaaagat     120
tttctggaag tgaccttcga tggcggtaaa atggttcagg tggtttatga ttaccagcat     180
aaagaaggcc gctttaaaag ccaggatgcc gattatcacc gtgtgatgta cgcatctagt     240
ggtatcggtc cagaaaaagc gttccgcgaa ctggccgatg cactgctgga aaaaggtaac     300
ccggaaatgg ttgatgtggt tacgggcgcg accgtgagct ctcagagttt tcgtcgcctg     360
ggtcgtgccc tgctgcagag cgcacgccgt ggcgaaaaag aagccattat ctctcgcggt     420
agatccgtga gctgcaccac ggtttgtccg catgcgggca agccaaagc agaaaaagtg      480
gaatgcgcgc tgaaaggtgg cattttttcgt ggtaccctgc cggccgcaga ttgtccgggc     540
atcgatacga ccgttacgtt caacgcggat ggtaccgccc agaaagtgga actggcactg     600
gaaaagaaaa gcgcgccgag tccgctgacg tatcgcggca cctggatggt tcgtgaagat     660
ggtattgtgg aactgagcct ggtttctagt gaacagagca agccccgca cgaaaaagaa      720
ctgtacgaac tgatcgattc taatagcgtg cgctatatgg gcgcaccggg tgcgggcaaa     780
ccgagcaaag aaatggcccc gttttacgtt ctgaagaaaa ccaagaaagg cccgagatcc     840
ggcagctctc atcacgaaac ccattatggt tacgcgacgc tgagttatgc cgattactgg     900
gcaggcgaac tgggtcagag ccgtgatgtg ctgctgcgcg caacgccga agcagatcgc      960
gcgggtgatc tggatgccgg catgtttgat gcagtttctc gtcgacccca cggtcatggc    1020
gccttccgcc agcagtttca gtatgcagtg gaagttctgg gtgaaaaagt gctgagtaaa    1080
caggaaacgg aagatagccg tggccgcaaa aaatgggaat acgaaaccga tccgtctgtt    1140
acgaaaatgg tgcgtgcgag tgccagcttc aggatctgg gtgaagatgg cgaaattaaa    1200
```

-continued

```
tttgaagcag ttgaaggtgc ggtggccctg gcagatcgcg cgtctagttt catggttgat   1260
agcgaagaat ataaaatcac caatgtgaaa gttcacggca tgaaatttgt gccggttgcc   1320
gtgccgcatg aactgaaagg tattgcaaaa gaaaaattcc actttgttga agattctcgt   1380
gtgacggaaa acaccaatgg cctgaaaacg atgctgaccg aagatagttt cagcgcgcgc   1440
aaagtttcta gtatggaaag cccgcatgat ctggtggttg atacggtggg taccggctac   1500
cactctcgtt ttggtagtga tgccgaagca agcgttatgc tgaaacgcgc ggatggctct   1560
gaactgagtc atcgtgaatt tatcgattat gtgatgaact ttaatacggt tcgctacgat   1620
tattacggtg atgatgccag ctataccaac ctgatggcat cttacggcac gaaacacagt   1680
gcggattctt ggtggaaaac cggtcgtgtg ccgcgcattt cttgcggcat caattatggt   1740
ttcgatcgtt ttaaaggcag cggtccgggc tactatcgcc tgacgctgat tgccaacggt   1800
taccgtgatg ttgtggcaga tgttcgcttc ctgccgaaat atgaaggcaa tatcgatatt   1860
ggtctgaaag gcaaagtgct gaccatcggt ggcgcggatg ccgaaaccct gatggatgca   1920
gccgttgatg tgtttgcgga tggtcagccg aaactggtta gcgatcaggc cgtgagcctg   1980
ggccagaacg ttctgagcgc ggatttcacc ccgggtaccg aatataccgt ggaagttcgt   2040
tttaaagaat ttggcagcgt gcgcgcgaaa gtggtggcgc agctcgcgac caaagccgtc   2100
agcgtgctga aggcgatgg tccggttcag ggtatcatca acttcgaaca aaaagaaagc   2160
aatggtccgg ttaaagtctg ggctctatt aaaggtctga cggaaggcct gcatggtttt   2220
catgtccacg aatttggcga caacaccgca ggttgcacga gtgctggccc gcatttcaat   2280
ccgctgtcac gtaaacacgg cggtccgaaa gatgaagaac gccacgtcgg cgacctgggt   2340
aacgtgaccg cagataaaga cggtgtggct gatgttagta ttgaagactc cgtgatcagc   2400
ctgtctggtg atcattccat tatcggccgt accctggtgg tgcacgaaaa agcagatgac   2460
ctgggcaaag gcggtaacga agaatcaacc aaaacgggta atgcaggttc gcgtctggca   2520
tgtggcgtta ttggtatcgc ccag                                          2544
```

<210> SEQ ID NO 2
<211> LENGTH: 2538
<212> TYPE: DNA
<213> ORGANISM: Treponema pallidum

<400> SEQUENCE: 2

```
atgcgtggat ctgctgtgcc gcctcaacag tgggccttgt ctggatccag cttttctagt     60
attccgaacg gcacctatcg tgcgacgtac caggatttcg atgaaaatgg ttggaaagat    120
tttctggaag tgaccttcga tggcggtaaa atggttcagg tggtttatga ttaccagcat    180
aaagaaggcc gctttaaaag ccaggatgcc gattatcacc gtgtgatgta cgcatctagt    240
ggtatcggtc cagaaaaagc gttccgcgaa ctggccgatg cactgctgga aaaaggtaac    300
ccggaaatgg ttgatgtggt tacgggcgcg accgtgagct ctcagagttt tcgtcgcctg    360
ggtcgtgccc tgctgcagag cgcacgccgt ggcgaaaaag aagccattat ctctcgcggt    420
agatccggca gctctcatca cgaaacccat tatggttacg cgacgctgag ttatgccgat    480
tactgggcag gcgaactggg tcagagccgt gatgtgctgc tggcgggcaa cgccgaagca    540
gatcgcgcgg gtgatctgga tgccggcatg tttgatgcag tttctcgtgc gacccacggt    600
catggcgcct tccgccagca gtttcagtat gcagtggaag ttctgggtga aaaagtgctg    660
agtaaacagg aaacggaaga tagccgtggc cgcaaaaaat gggaatacga aaccgatccg    720
```

```
tctgttacga aaatggtgcg tgcgagtgcc agcttccagg atctgggtga agatggcgaa     780
attaaatttg aagcagttga aggtgcggtg gccctggcag atcgcgcgtc tagtttcatg     840
gttgatagcg aagaatataa aatcaccaat gtgaaagttc acggcatgaa atttgtgccg     900
gttgccgtgc cgcatgaact gaaaggtatt gcaaaagaaa aattccactt tgttgaagat     960
tctcgtgtga cggaaaacac caatggcctg aaaacgatgc tgaccgaaga tagtttcagc    1020
gcgcgcaaag tttctagtat ggaaagcccc catgatctgg tggttgatac ggtgggtacc    1080
ggctaccact ctcgttttgg tagtgatgcc gaagcaagcg ttatgctgaa acgcgcggat    1140
ggctctgaac tgagtcatcg tgaatttatc gattatgtga tgaactttaa tacggttcgc    1200
tacgattatt acggtgatga tgccagctat accaacctga tggcatctta cggcacgaaa    1260
cacagtgcgg attcttggtg aaaaccggt cgtgtgccgc gcatttcttg cggcatcaat    1320
tatggtttcg atcgttttaa aggcagcggt ccgggctact atcgcctgac gctgattgcc    1380
aacggttacc gtgatgttgt ggcagatgtt cgcttcctgc cgaaatatga aggcaatatc    1440
gatattggtc tgaaaggcaa agtgctgacc atcggtggcg cggatgccga aaccctgatg    1500
gatgcagccg ttgatgtgtt tgcggatggt cagccgaaac tggttagcga tcaggccgtg    1560
agcctgggcc agaacgttct gagcgcggat ttcaccccgg gtaccgaata taccgtggaa    1620
gttcgtttta agaatttgg cagcgtgcgc gcgaaagtgg tggcgcaggg gcccgtgagc    1680
tgcaccacgg tttgtccgca tgcgggcaaa gccaaagcag aaaaagtgga atgcgcgctg    1740
aaaggtggca ttttcgtgg taccctgccg gccgcagatt gtccgggcat cgatacgacc    1800
gttacgttca acgcggatgg taccgcccag aaagtgaaac tggcactgga aaagaaaagc    1860
gcgccgagtc cgctgacgta tcgcggcacc tggatggttc gtgaagatgg tattgtggaa    1920
ctgagcctgt tttctagtga acagagcaaa gccccgcacg aaaaagaact gtacgaactg    1980
atcgattcta atagcgtgcg ctatatgggc gcaccgggtg cgggcaaacc gagcaaagaa    2040
atggccccgt tttacgttct gaagaaaacc aagaaactcg cgaccaaagc cgtcagcgtg    2100
ctgaaaggcg atggtccggt tcagggtatc atcaacttcg aacaaaaaga aagcaatggt    2160
ccggttaaag tctggggctc tattaaaggt ctgacggaag gcctgcatgg ttttcatgtc    2220
cacgaatttg gcgacaacac cgcaggttgc acgagtgctg gcccgcattt caatccgctg    2280
tcacgtaaac acggcggtcc gaaagatgaa gaacgccacg tcggcgacct gggtaacgtg    2340
accgcagata aagacggtgt ggctgatgtt agtattgaag actccgtgat cagcctgtct    2400
ggtgatcatt ccattatcgg ccgtaccctg gtggtgcacg aaaaagcaga tgacctgggc    2460
aaaggcggta acgaagaatc aaccaaaacg ggtaatgcag gttcgcgtct ggcatgtggc    2520
gttattggta tcgcccag                                                   2538

<210> SEQ ID NO 3
<211> LENGTH: 2547
<212> TYPE: DNA
<213> ORGANISM: Treponema pallidum

<400> SEQUENCE: 3
atgcgtggat ctgctgtgcc gcctcaacag tgggccttgt ctggatccgt gagctgcacc      60
acggtttgtc cgcatgcggg caaagccaaa gcagaaaaag tggaatgcgc gctgaaaggt     120
ggcattttc gtggtaccct gccggccgca gattgtccgg catcgatac gaccgttacg     180
ttcaacgcgg atggtaccgc ccagaaagtg aactggcac tggaaaagaa aagcgcgccg     240
agtccgctga cgtatcgcgg cacctggatg gttcgtgaag atggtattgt ggaactgagc     300
```

```
ctggtttcta gtgaacagag caaagccccg cacgaaaaag aactgtacga actgatcgat    360
tctaatagcg tgcgctacat gggcgcaccg ggtgcgggca aaccgagcaa agaaatggcc    420
ccgttttacg ttctgaagaa aaccaagaaa ggcccgagat ccagcttttc tagtattccg    480
aacggcacct atcgtgcgac gtaccaggat ttcgatgaaa atggttggaa agattttctg    540
gaagtgacct tcgatggcgg taaaatggtt caggtggttt atgattacca gcataaagaa    600
ggccgcttta aaagccagga tgccgattat caccgtgtga tgtacgcatc tagtggtatc    660
ggtccagaaa aagcgttccg cgaactggcc gatgcactgc tggaaaaagg taacccggaa    720
atggttgatg tggttacggg cgcgaccgtg agctctcaga gttttcgtcg cctgggtcgt    780
gccctgctgc agagcgcacg ccgtggcgaa aaagaagcca ttatctctcg cggcccgaga    840
tccggcagct ctcatcacga aacccattat ggttacgcga cgctgagtta tgccgattac    900
tgggcaggcg aactgggtca gagccgtgat gtgctgctgg cgggcaacgc cgaagcagat    960
cgcgcgggtg atctgatgc cggcatgttt gatgcagttt ctcgtgcgac ccacggtcat   1020
ggcgccttcc gccagcagtt tcagtatgca gtggaagttc tgggtgaaaa agtgctgagt   1080
aaacaggaaa cggaagatag ccgtggccgc aaaaaatggg aatacgaaac cgatccgtct   1140
gttacgaaaa tggtgcgtgc gagtgccagc ttccaggatc tgggtgaaga tggcgaaatt   1200
aaatttgaag cagttgaagg tgcggtggcc ctggcagatc gcgcgtctag tttcatggtt   1260
gatagcgaag aatataaaat caccaatgtg aaagttcacg gcatgaaatt tgtgccggtt   1320
gccgtgccgc atgaactgaa aggtattgca aaagaaaaat tccactttgt tgaagattct   1380
cgtgtgacgg aaaacaccaa tggcctgaaa acgatgctga ccgaagatag tttcagcgcg   1440
cgcaaagttt ctagtatgga aagcccgcat gatctggtgg ttgatacggt gggtaccggc   1500
taccactctc gttttggtag tgatgccgaa gcaagcgtta tgctgaaacg cgcggatggc   1560
tctgaactga gtcatcgtga atttatcgat tatgtgatga ctttaatac ggttcgctac   1620 gattattacg gtgatgatgc cagctatacc aacctgatgg catcttacgg cacgaaacac   1680
agtgcggatt cttggtggaa aaccggtcgt gtgccgcgca tttcttgcgg catcaattat   1740
ggtttcgatc gttttaaagg cagcggtccg ggctactatc gcctgacgct gattgccaac   1800
ggttaccgtg atgttgtggc agatgttcgc ttcctgccga aatatgaagg caatatcgat   1860
attggtctga aggcaaagt gctgaccatc ggtggcgcgg atgccgaaac cctgatggat   1920
gcagccgttg atgtgtttgc ggatggtcag ccgaaactgg ttagcgatca ggccgtgagc   1980
ctgggccaga acgttctgag cgcggatttc accccgggta ccgaatatac cgtggaagtt   2040
cgttttaaag aatttggcag cgtgcgcgcg aaagtggtgg cgcagctcgc gaccaaagcc   2100
gtcagcgtgc tgaaaggcga tggtccggtt cagggtatca tcaacttcga acaaaaagaa   2160
agcaatggtc cggttaaagt ctggggctct attaaaggtc tgacggaagg cctgcatggt   2220
tttcatgtcc acgaatttgg cgacaacacc gcaggttgca cgagtgctgg cccgcatttc   2280
aatccgctgt cacgtaaaca cggcggtccg aaagatgaag aacgccacgt cggcgacctg   2340
ggtaacgtga ccgcagataa agacggtgtg gctgatgtta gtattgaaga ctccgtgatc   2400
agcctgtctg tgatcattc cattatcggc cgtaccctgg tggtgcacga aaaagcagat   2460
gacctgggca aaggcggtaa cgaagaatca accaaaacgg gtaatgcagg ttcgcgtctg   2520
gcatgtggcg ttattggtat cgcccag                                      2547
```

<210> SEQ ID NO 4

-continued

<211> LENGTH: 2541
<212> TYPE: DNA
<213> ORGANISM: Treponema pallidum

<400> SEQUENCE: 4
atgcgtggat ctgctgtgcc gcctcaacag tgggccttgt ctggatccgt gagctgcacc 60
acggtttgtc cgcatgcggg caaagccaaa gcagaaaaag tggaatgcgc gctgaaaggt 120
ggcatttttc gtggtaccct gccggccgca gattgtccgg gcatcgatac gaccgttacg 180
ttcaacgcgg atggtaccgc ccagaaagtg gaactggcac tggaaaagaa aagcgcgccg 240
agtccgctga cgtatcgcgg cacctggatg gttcgtgaag atggtattgt ggaactgagc 300
ctggtttcta gtgaacagag caaagccccg cacgaaaaag aactgtacga actgatcgat 360
tctaatagcg tgcgctatat gggcgcaccg ggtgcgggca aaccgagcaa agaaatggcc 420
ccgttttacg ttctgaagaa aaccaagaaa ggcccgagat ccggcagctc tcatcacgaa 480
acccattatg gttacgcgac gctgagttat gccgattact gggcaggcga actgggtcag 540
agccgtgatg tgctgctggc gggcaacgcc gaagcagatc gcgcgggtga tctggatgcc 600
ggcatgtttg atgcagtttc tcgtgcgacc cacggtcatg gcgccttccg ccagcagttt 660
cagtatgcag tggaagttct gggtgaaaaa gtgctgagta aacaggaaac ggaagatagc 720
cgtggccgca aaaaatggga atacgaaacc gatccgtctg ttacgaaaat ggtgcgtgcg 780
agtgccagct tccaggatct gggtgaagat ggcgaaatta aatttgaagc agttgaaggt 840
gcggtggccc tggcagatcg cgcgtctagt ttcatggttg atagcgaaga atataaaatc 900
accaatgtga aagttcacgg catgaaattt gtgccggttg ccgtgccgca tgaactgaaa 960
ggtattgcaa aagaaaaatt ccactttgtt gaagattctc gtgtgacgga aaacaccaat 1020
ggcctgaaaa cgatgctgac cgaagatagt ttcagcgcgc gcaaagtttc tagtatggaa 1080
agcccgcatg atctggtggt tgatacggtg ggtaccggct accactctcg ttttggtagt 1140
gatgccgaag caagcgttat gctgaaacgc gcggatggct ctgaactgag tcatcgtgaa 1200
tttatcgatt atgtgatgaa ctttaatacg gttcgctacg attattacgg tgatgatgcc 1260
agctatacca acctgatggc atcttacggc acgaaacaca gtgcggattc ttggtggaaa 1320
accggtcgtg tgccgcgcat ttcttgcggc atcaattatg gtttcgatcg ttttaaaggc 1380
agcggtccgg gctactatcg cctgacgctg attgccaacg gttaccgtga tgttgtggca 1440
gatgttcgct tcctgccgaa atatgaaggc aatatcgata ttggtctgaa aggcaaagtg 1500
ctgaccatcg gtggcgcgga tgccgaaacc ctgatggatg cagccgttga tgtgtttgcg 1560
gatggtcagc cgaaactggt tagcgatcag gccgtgagcc tgggccagaa cgttctgagc 1620
gcggatttca ccccgggtac cgaatatacc gtggaagttc gttttaaaga atttggcagc 1680
gtgcgcgcga aagtggtggc gcaggggccc agcttttcta gtattccgaa cggcacctat 1740
cgtgcgacgt accaggattt cgatgaaaat ggttggaaag attttctgga agtgaccttc 1800
gatggcggta aaatggttca ggtggtttat gattaccagc ataaagaagg ccgctttaaa 1860
agccaggatg ccgattatca ccgtgtgatg tacgcatcta gtggtatcgg tccagaaaaa 1920
gcgttccgcg aactggccga tgcactgctg gaaaaaggta acccggaaat ggttgatgtg 1980
gttacgggcg cgaccgtgag ctctcagagt tttcgtcgcc tgggtcgtgc cctgctgcag 2040
agcgcacgcc gtggcgaaaa agaagccatt atctctcgcc tcgcgaccaa agccgtcagc 2100
gtgctgaaag gcgatggtcc ggttcagggt atcatcaact tcgaacaaaa agaaagcaat 2160
ggtccggtta aagtctgggg ctctattaaa ggtctgacgg aaggcctgca tggttttcat 2220

| | |
|---|---:|
| gtccacgaat ttggcgacaa caccgcaggt tgcacgagtg ctggcccgca tttcaatccg | 2280 |
| ctgtcacgta aacacggcgg tccgaaagat gaagaacgcc acgtcggcga cctgggtaac | 2340 |
| gtgaccgcag ataaagacgg tgtggctgat gttagtattg aagactccgt gatcagcctg | 2400 |
| tctggtgatc attccattat cggccgtacc ctggtggtgc acgaaaaagc agatgacctg | 2460 |
| ggcaaaggcg gtaacgaaga atcaaccaaa acgggtaatg caggttcgcg tctggcatgt | 2520 |
| ggcgttattg gtatcgccca g | 2541 |

<210> SEQ ID NO 5
<211> LENGTH: 2541
<212> TYPE: DNA
<213> ORGANISM: Treponema pallidum

<400> SEQUENCE: 5

| | |
|---|---:|
| atgcgtggat ctgctgtgcc gcctcaacag tgggccttgt ctggatccgg cagctctcat | 60 |
| cacgaaaccc attatggtta cgcgacgctg agttatgccg attactgggc aggcgaactg | 120 |
| ggtcagagcc gtgatgtgct gctggcgggc aacgccgaag cagatcgcgc gggtgatctg | 180 |
| gatgccggca tgtttgatgc agtttctcgt gcgacccacg tcatggcgc cttccgccag | 240 |
| cagtttcagt atgcagtgga agttctgggt gaaaagtgc tgagtaaaca ggaaacggaa | 300 |
| gatagccgtg ccgcaaaaa atgggaatac gaaaccgatc cgtctgttac gaaaatggtg | 360 |
| cgtgcgagtg ccagcttcca ggatctgggt gaagatggcg aaattaaatt tgaagcagtt | 420 |
| gaaggtgcgg tggccctggc agatcgcgcg tctagtttca tggttgatag cgaagaatat | 480 |
| aaaatcacca atgtgaaagt tcacggcatg aaatttgtgc cggttgccgt gccgcatgaa | 540 |
| ctgaaaggta ttgcaaaaga aaaattccac tttgttgaag attctcgtgt gacggaaaac | 600 |
| accaatggcc tgaaaacgat gctgaccgaa gatagtttca gcgcgcgcaa agtttctagt | 660 |
| atggaaagcc gcatgatct ggtggttgat acgtgggta ccggctacca ctctcgtttt | 720 |
| ggtagtgatg ccgaagcaag cgttatgctg aaacgcgcgg atggctctga actgagtcat | 780 |
| cgtgaattta tcgattatgt gatgaacttt aatacggttc gctacgatta ttacggtgat | 840 |
| gatgccagct ataccaacct gatggcatct tacggcacga aacacagtgc ggattcttgg | 900 |
| tggaaaaccg tcgtgtgcc gcgcattct tgcggcatca attatggttt cgatcggttt | 960 |
| aaaggcagcg gtccgggcta ctatcgcctg acgctgattg ccaacggtta ccgtgatgtt | 1020 |
| gtggcagatg ttcgcttcct gccgaaatat gaaggcaata tcgatattgg tctgaaaggc | 1080 |
| aaagtgctga ccatcggtgg cgcggatgcc gaaaccctga tggatgcagc cgttgatgtg | 1140 |
| tttgcggatg gtcagccgaa actggttagc gatcaggccg tgagcctggg ccagaacgtt | 1200 |
| ctgagcgcg atttccaccc gggtaccgaa tataccgtgg aagttcgttt taagaatttt | 1260 |
| ggcagcgtgc gcgcgaaagt ggtggcgcag gtccaagat ccagcttttc tagtattccg | 1320 |
| aacggcacct atcgtgcgac gtaccaggat ttcgatgaaa atggttggaa agattttctg | 1380 |
| gaagtgacct tcgatggcgg taaaatggtt caggtggttt atgattacca gcataaagaa | 1440 |
| ggccgcttta aaagccagga tgccgattat caccgtgtga tgtacgcatc tagtggtatc | 1500 |
| ggtccagaaa aagcgttccg cgaactggcc gatgcactgc tggaaaaagg taacccggaa | 1560 |
| atggttgatg tggttacggg cgcgaccgtg agctctcaga gttttcgtcg cctgggtcgt | 1620 |
| gccctgctgc agagcgcacg ccgtggcgaa aagaagcca ttatctctcg cgggcccgtg | 1680 |
| agctgcacca cggtttgtcc gcatgcgggc aaagccaaag cagaaaaagt ggaatgcgcg | 1740 |

-continued

```
ctgaaaggtg gcatttttcg tggtaccctg ccggccgcag attgtccggg catcgatacg   1800
accgttacgt tcaacgcgga tggtaccgcc cagaaagtgg aactggcact ggaaaagaaa   1860
agcgcgccga gtccgctgac gtatcgcggc acctggatgg ttcgtgaaga tggtattgtg   1920
gaactgagcc tggtttctag tgaacagagc aaagccccgc acgaaaaaga actgtacgaa   1980
ctgatcgatt ctaatagcgt gcgctatatg ggcgcaccgg gtgcgggcaa accgagcaaa   2040
gaaatggccc cgttttacgt tctgaagaaa accaagaaac tcgcgaccaa agccgtcagc   2100
gtgctgaaag gcgatggtcc ggttcagggt atcatcaact tcgaacaaaa agaaagcaat   2160
ggtccggtta aagtctgggg ctctattaaa ggtctgacgg aaggcctgca tggttttcat   2220
gtccacgaat ttggcgacaa caccgcaggt tgcacgagtg ctggcccgca tttcaatccg   2280
ctgtcacgta aacacggcgg tccgaaagat gaagaacgcc acgtcggcga cctgggtaac   2340
gtgaccgcag ataaagacgg tgtggctgat gttagtattg aagactccgt gatcagcctg   2400
tctggtgatc attccattat cggccgtacc ctggtggtgc acgaaaaagc agatgacctg   2460
ggcaaaggcg gtaacgaaga atcaaccaaa acgggtaatg caggttcgcg tctggcatgt   2520
ggcgttattg gtatcgccca g                                             2541
```

<210> SEQ ID NO 6
<211> LENGTH: 2547
<212> TYPE: DNA
<213> ORGANISM: Treponema pallidum

<400> SEQUENCE: 6

```
atgcgtggat ctgctgtgcc gcctcaacag tgggccttgt ctggatccgg cagctctcat     60
cacgaaaccc attatggtta cgcgacgctg agttatgccg attactgggc aggcgaactg    120
ggtcagagcc gtgatgtgct gctggcgggc aacgccgaag cagatcgcgc gggtgatctg    180
gatgccggca tgtttgatgc agtttctcgt gcgacccacg gtcatggcgc cttccgccag    240
cagtttcagt atgcagtgga agttctgggt gaaaaagtgc tgagtaaaca ggaaacggaa    300
gatagccgtg gccgcaaaaa atgggaatac gaaaccgatc cgtctgttac gaaaatggtg    360
cgtgcgagtg ccagcttcca ggatctgggt gaagatggcg aaattaaatt tgaagcagtt    420
gaaggtgcgg tggccctggc agatcgcgcg tctagtttca tggttgatag cgaagaatat    480
aaaatcacca atgtgaaagt tcacggcatg aaatttgtgc cggttgccgt gccgcatgaa    540
ctgaaaggta ttgcaaaaga aaaattccac tttgttgaag attctcgtgt gacggaaaac    600
accaatggcc tgaaaacgat gctgaccgaa gatagtttca gcgcgcgcaa agtttctagt    660
atggaaagcc cgcatgatct ggtggttgat acggtgggta ccggctacca ctctcgtttt    720
ggtagtgatg ccgaagcaag cgttatgctg aaacgcgcgg atggctctga actgagtcat    780
cgtgaattta tcgattatgt gatgaacttt aatacggttc gctacgatta ttacggtgat    840
gatgccagct ataccaacct gatggcatct tacggcacga aacacagtgc ggattcttgg    900
tggaaaaccg gtcgtgtgcc gcgcatttct tgcggcatca attatggttt cgatcggttt    960
aaaggcagcg gtccgggcta ctatcgcctg acgctgattg ccaacggtta ccgtgatgtt   1020
gtggcagatg ttcgcttcct gccgaaatat gaaggcaata tcgatattgg tctgaaaggc   1080
aaagtgctga ccatcggtgg cgcggatgcc gaaaccctga tggatgcagc cgttgatgtg   1140
tttgcggatg gtcagccgaa actggttagc gatcaggccg tgagcctggg ccagaacgtt   1200
ctgagcgcgg atttcacccc gggtaccgaa tataccgtgg aagttcgttt taaagaattt   1260
ggcagcgtgc gcgcgaaagt ggtggcgcag ggcccgagat ccgtgagctg caccacggtt   1320

```
tgtccgcatg cgggcaaagc caaagcagaa aaagtggaat gcgcgctgaa aggtggcatt    1380
tttcgtggta ccctgccggc cgcagattgt ccgggcatcg atacgaccgt tacgttcaac    1440
gcggatggta ccgcccagaa agtggaactg gcactggaaa agaaaagcgc gccgagtccg    1500
ctgacgtatc gcggcacctg gatggttcgt gaagatggta ttgtggaact gagcctggtt    1560
tctagtgaac agagcaaagc cccgcacgaa aaagaactgt acgaactgat cgattctaat    1620
agcgtgcgct acatgggcgc accgggtgcg ggcaaaccga gcaaagaaat ggccccgttt    1680
tacgttctga agaaaaccaa gaaaggcccg agatccagct tttctagtat tccgaacggc    1740
acctatcgtg cgacgtacca ggatttcgat gaaaatggtt ggaaagattt tctggaagtg    1800
accttcgatg gcggtaaaat ggttcaggtg gtttatgatt accagcataa agaaggccgc    1860
tttaaaagcc aggatgccga ttatcaccgt gtgatgtacg catctagtgg tatcggtcca    1920
gaaaaagcgt tccgcgaact ggccgatgca ctgctggaaa aaggtaaccc ggaaatggtt    1980
gatgtggtta cgggcgcgac cgtgagctct cagagttttc gtcgcctggg tcgtgccctg    2040
ctgcagagcg cacgccgtgg cgaaaaagaa gccattatct ctcgcctcgc gaccaaagcc    2100
gtcagcgtgc tgaaaggcga tggtccggtt cagggtatca tcaacttcga acaaaaagaa    2160
agcaatggtc cggttaaagt ctggggctct attaaaggtc tgacggaagg cctgcatggt    2220
tttcatgtcc acgaatttgg cgacaacacc gcaggttgca cgagtgctgg cccgcatttc    2280
aatccgctgt cacgtaaaca cggcggtccg aaagatgaag aacgccacgt cggcgacctg    2340
ggtaacgtga ccgcagataa agacggtgtg gctgatgtta gtattgaaga ctccgtgatc    2400
agcctgtctg gtgatcattc cattatcggc cgtaccctgg tggtgcacga aaaagcagat    2460
gacctgggca aggcggtaa cgaagaatca accaaaacgg gtaatgcagg ttcgcgtctg    2520
gcatgtggcg ttattggtat cgcccag                                       2547
```

<210> SEQ ID NO 7
<211> LENGTH: 848
<212> TYPE: PRT
<213> ORGANISM: Treponema pallidum
<220> FEATURE:
<221> NAME/KEY: MISC_FEATURE
<222> LOCATION: (5)..(14)
<223> OTHER INFORMATION: 261 tag
<220> FEATURE:
<221> NAME/KEY: MISC_FEATURE
<222> LOCATION: (17)..(139)
<223> OTHER INFORMATION: Treponema pallidum outer membrane protein TP15
<220> FEATURE:
<221> NAME/KEY: MISC_FEATURE
<222> LOCATION: (143)..(276)
<223> OTHER INFORMATION: Treponema pallidum outer membrane protein TP17
<220> FEATURE:
<221> NAME/KEY: MISC_FEATURE
<222> LOCATION: (281)..(694)
<223> OTHER INFORMATION: Treponema pallidum outer membrane protein TP47
<220> FEATURE:
<221> NAME/KEY: MISC_FEATURE
<222> LOCATION: (696)..(848)
<223> OTHER INFORMATION: human copper zinc superoxide dismutase

<400> SEQUENCE: 7

```
Met Arg Gly Ser Ala Val Pro Pro Gln Gln Trp Ala Leu Ser Gly Ser
1               5                   10                  15

Ser Phe Ser Ser Ile Pro Asn Gly Thr Tyr Arg Ala Thr Tyr Gln Asp
            20                  25                  30

Phe Asp Glu Asn Gly Trp Lys Asp Phe Leu Glu Val Thr Phe Asp Gly
        35                  40                  45
```

```
Gly Lys Met Val Gln Val Val Tyr Asp Tyr Gln His Lys Glu Gly Arg
     50                  55                  60

Phe Lys Ser Gln Asp Ala Asp Tyr His Arg Val Met Tyr Ala Ser Ser
 65                  70                  75                  80

Gly Ile Gly Pro Glu Lys Ala Phe Arg Glu Leu Ala Asp Ala Leu Leu
                 85                  90                  95

Glu Lys Gly Asn Pro Glu Met Val Asp Val Val Thr Gly Ala Thr Val
             100                 105                 110

Ser Ser Gln Ser Phe Arg Arg Leu Gly Arg Ala Leu Leu Gln Ser Ala
         115                 120                 125

Arg Arg Gly Glu Lys Glu Ala Ile Ile Ser Arg Gly Arg Ser Val Ser
    130                 135                 140

Cys Thr Thr Val Cys Pro His Ala Gly Lys Ala Lys Ala Glu Lys Val
145                 150                 155                 160

Glu Cys Ala Leu Lys Gly Gly Ile Phe Arg Gly Thr Leu Pro Ala Ala
                165                 170                 175

Asp Cys Pro Gly Ile Asp Thr Thr Val Thr Phe Asn Ala Asp Gly Thr
            180                 185                 190

Ala Gln Lys Val Glu Leu Ala Leu Glu Lys Lys Ser Ala Pro Ser Pro
        195                 200                 205

Leu Thr Tyr Arg Gly Thr Trp Met Val Arg Glu Asp Gly Ile Val Glu
    210                 215                 220

Leu Ser Leu Val Ser Ser Glu Gln Ser Lys Ala Pro His Glu Lys Glu
225                 230                 235                 240

Leu Tyr Glu Leu Ile Asp Ser Asn Ser Val Arg Tyr Met Gly Ala Pro
                245                 250                 255

Gly Ala Gly Lys Pro Ser Lys Glu Met Ala Pro Phe Tyr Val Leu Lys
            260                 265                 270

Lys Thr Lys Lys Gly Pro Arg Ser Gly Ser His His Glu Thr His
        275                 280                 285

Tyr Gly Tyr Ala Thr Leu Ser Tyr Ala Asp Tyr Trp Ala Gly Glu Leu
    290                 295                 300

Gly Gln Ser Arg Asp Val Leu Leu Ala Gly Asn Ala Glu Ala Asp Arg
305                 310                 315                 320

Ala Gly Asp Leu Asp Ala Gly Met Phe Asp Ala Val Ser Arg Ala Thr
                325                 330                 335

His Gly His Gly Ala Phe Arg Gln Gln Phe Gln Tyr Ala Val Glu Val
            340                 345                 350

Leu Gly Glu Lys Val Leu Ser Lys Gln Glu Thr Glu Asp Ser Arg Gly
        355                 360                 365

Arg Lys Lys Trp Glu Tyr Glu Thr Asp Pro Ser Val Thr Lys Met Val
    370                 375                 380

Arg Ala Ser Ala Ser Phe Gln Asp Leu Gly Glu Asp Gly Glu Ile Lys
385                 390                 395                 400

Phe Glu Ala Val Glu Gly Ala Val Ala Leu Ala Asp Arg Ala Ser Ser
                405                 410                 415

Phe Met Val Asp Ser Glu Glu Tyr Lys Ile Thr Asn Val Lys Val His
            420                 425                 430

Gly Met Lys Phe Val Pro Val Ala Val Pro His Glu Leu Lys Gly Ile
        435                 440                 445

Ala Lys Glu Lys Phe His Phe Val Glu Asp Ser Arg Val Thr Glu Asn
    450                 455                 460
```

```
Thr Asn Gly Leu Lys Thr Met Leu Thr Glu Asp Ser Phe Ser Ala Arg
465                 470                 475                 480

Lys Val Ser Ser Met Glu Ser Pro His Asp Leu Val Val Asp Thr Val
            485                 490                 495

Gly Thr Gly Tyr His Ser Arg Phe Gly Ser Asp Ala Glu Ala Ser Val
        500                 505                 510

Met Leu Lys Arg Ala Asp Gly Ser Glu Leu Ser His Arg Glu Phe Ile
            515                 520                 525

Asp Tyr Val Met Asn Phe Asn Thr Val Arg Tyr Asp Tyr Tyr Gly Asp
530                 535                 540

Asp Ala Ser Tyr Thr Asn Leu Met Ala Ser Tyr Gly Thr Lys His Ser
545                 550                 555                 560

Ala Asp Ser Trp Trp Lys Thr Gly Arg Val Pro Arg Ile Ser Cys Gly
            565                 570                 575

Ile Asn Tyr Gly Phe Asp Arg Phe Lys Gly Ser Gly Pro Gly Tyr Tyr
            580                 585                 590

Arg Leu Thr Leu Ile Ala Asn Gly Tyr Arg Asp Val Val Ala Asp Val
        595                 600                 605

Arg Phe Leu Pro Lys Tyr Glu Gly Asn Ile Asp Ile Gly Leu Lys Gly
610                 615                 620

Lys Val Leu Thr Ile Gly Gly Ala Asp Ala Glu Thr Leu Met Asp Ala
625                 630                 635                 640

Ala Val Asp Val Phe Ala Asp Gly Gln Pro Lys Leu Val Ser Asp Gln
            645                 650                 655

Ala Val Ser Leu Gly Gln Asn Val Leu Ser Ala Asp Phe Thr Pro Gly
            660                 665                 670

Thr Glu Tyr Thr Val Glu Val Arg Phe Lys Glu Phe Gly Ser Val Arg
            675                 680                 685

Ala Lys Val Val Ala Gln Leu Ala Thr Lys Ala Val Ser Val Leu Lys
        690                 695                 700

Gly Asp Gly Pro Val Gln Gly Ile Ile Asn Phe Glu Gln Lys Glu Ser
705                 710                 715                 720

Asn Gly Pro Val Lys Val Trp Gly Ser Ile Lys Gly Leu Thr Glu Gly
            725                 730                 735

Leu His Gly Phe His Val His Glu Phe Gly Asp Asn Thr Ala Gly Cys
            740                 745                 750

Thr Ser Ala Gly Pro His Phe Asn Pro Leu Ser Arg Lys His Gly Gly
            755                 760                 765

Pro Lys Asp Glu Glu Arg His Val Gly Asp Leu Gly Asn Val Thr Ala
            770                 775                 780

Asp Lys Asp Gly Val Ala Asp Val Ser Ile Glu Asp Ser Val Ile Ser
785                 790                 795                 800

Leu Ser Gly Asp His Ser Ile Ile Gly Arg Thr Leu Val Val His Glu
            805                 810                 815

Lys Ala Asp Asp Leu Gly Lys Gly Gly Asn Glu Glu Ser Thr Lys Thr
            820                 825                 830

Gly Asn Ala Gly Ser Arg Leu Ala Cys Gly Val Ile Gly Ile Ala Gln
            835                 840                 845
```

<210> SEQ ID NO 8
<211> LENGTH: 846
<212> TYPE: PRT
<213> ORGANISM: Treponema pallidum
<220> FEATURE:
<221> NAME/KEY: MISC_FEATURE
<222> LOCATION: (5)..(14)
<223> OTHER INFORMATION: 261 tag
<220> FEATURE:
<221> NAME/KEY: MISC_FEATURE
<222> LOCATION: (17)..(139)
<223> OTHER INFORMATION: Treponema pallidum outer membrane protein TP15
<220> FEATURE:
<221> NAME/KEY: MISC_FEATURE
<222> LOCATION: (143)..(556)
<223> OTHER INFORMATION: Treponema pallidum outer membrane protein TP47
<220> FEATURE:
<221> NAME/KEY: MISC_FEATURE
<222> LOCATION: (559)..(692)
<223> OTHER INFORMATION: Treponema pallidum outer membrane protein TP17
<220> FEATURE:
<221> NAME/KEY: MISC_FEATURE
<222> LOCATION: (694)..(846)
<223> OTHER INFORMATION: human copper zinc superoxide dismutase

<400> SEQUENCE: 8

Met Arg Gly Ser Ala Val Pro Pro Gln Gln Trp Ala Leu Ser Gly Ser
 1               5                  10                  15

Ser Phe Ser Ser Ile Pro Asn Gly Thr Tyr Arg Ala Thr Tyr Gln Asp
                20                  25                  30

Phe Asp Glu Asn Gly Trp Lys Asp Phe Leu Glu Val Thr Phe Asp Gly
            35                  40                  45

Gly Lys Met Val Gln Val Val Tyr Asp Tyr Gln His Lys Glu Gly Arg
        50                  55                  60

Phe Lys Ser Gln Asp Ala Asp Tyr His Arg Val Met Tyr Ala Ser Ser
65                  70                  75                  80

Gly Ile Gly Pro Glu Lys Ala Phe Arg Glu Leu Ala Asp Ala Leu Leu
                85                  90                  95

Glu Lys Gly Asn Pro Glu Met Val Asp Val Val Thr Gly Ala Thr Val
            100                 105                 110

Ser Ser Gln Ser Phe Arg Arg Leu Gly Arg Ala Leu Leu Gln Ser Ala
        115                 120                 125

Arg Arg Gly Glu Lys Glu Ala Ile Ile Ser Arg Gly Arg Ser Gly Ser
    130                 135                 140

Ser His His Glu Thr His Tyr Gly Tyr Ala Thr Leu Ser Tyr Ala Asp
145                 150                 155                 160

Tyr Trp Ala Gly Glu Leu Gly Gln Ser Arg Asp Val Leu Leu Ala Gly
                165                 170                 175

Asn Ala Glu Ala Asp Arg Ala Gly Asp Leu Asp Ala Gly Met Phe Asp
            180                 185                 190

Ala Val Ser Arg Ala Thr His Gly His Gly Ala Phe Arg Gln Gln Phe
        195                 200                 205

Gln Tyr Ala Val Glu Val Leu Gly Glu Lys Val Leu Ser Lys Gln Glu
    210                 215                 220

Thr Glu Asp Ser Arg Gly Arg Lys Lys Trp Glu Tyr Glu Thr Asp Pro
225                 230                 235                 240

Ser Val Thr Lys Met Val Arg Ala Ser Ala Ser Phe Gln Asp Leu Gly
                245                 250                 255

Glu Asp Gly Glu Ile Lys Phe Glu Ala Val Glu Gly Ala Val Ala Leu
            260                 265                 270

Ala Asp Arg Ala Ser Ser Phe Met Val Asp Ser Glu Tyr Lys Ile
        275                 280                 285

Thr Asn Val Lys Val His Gly Met Lys Phe Val Pro Val Ala Val Pro
    290                 295                 300

His Glu Leu Lys Gly Ile Ala Lys Glu Lys Phe His Phe Val Glu Asp

```
            305                 310                 315                 320
        Ser Arg Val Thr Glu Asn Thr Asn Gly Leu Lys Thr Met Leu Thr Glu
                        325                 330                 335

Asp Ser Phe Ser Ala Arg Lys Val Ser Ser Met Glu Ser Pro His Asp
                        340                 345                 350

Leu Val Val Asp Thr Val Gly Thr Gly Tyr His Ser Arg Phe Gly Ser
                        355                 360                 365

Asp Ala Glu Ala Ser Val Met Leu Lys Arg Ala Asp Gly Ser Glu Leu
                    370                 375                 380

Ser His Arg Glu Phe Ile Asp Tyr Val Met Asn Phe Asn Thr Val Arg
        385                 390                 395                 400

Tyr Asp Tyr Tyr Gly Asp Ala Ser Tyr Thr Asn Leu Met Ala Ser
                        405                 410                 415

Tyr Gly Thr Lys His Ser Ala Asp Ser Trp Trp Lys Thr Gly Arg Val
                        420                 425                 430

Pro Arg Ile Ser Cys Gly Ile Asn Tyr Gly Phe Asp Arg Phe Lys Gly
                        435                 440                 445

Ser Gly Pro Gly Tyr Tyr Arg Leu Thr Leu Ile Ala Asn Gly Tyr Arg
                    450                 455                 460

Asp Val Val Ala Asp Val Arg Phe Leu Pro Lys Tyr Glu Gly Asn Ile
        465                 470                 475                 480

Asp Ile Gly Leu Lys Gly Lys Val Leu Thr Ile Gly Gly Ala Asp Ala
                        485                 490                 495

Glu Thr Leu Met Asp Ala Ala Val Asp Val Phe Ala Asp Gly Gln Pro
                        500                 505                 510

Lys Leu Val Ser Asp Gln Ala Val Ser Leu Gly Gln Asn Val Leu Ser
                    515                 520                 525

Ala Asp Phe Thr Pro Gly Thr Glu Tyr Thr Val Glu Val Arg Phe Lys
                    530                 535                 540

Glu Phe Gly Ser Val Arg Ala Lys Val Val Ala Gln Gly Pro Val Ser
        545                 550                 555                 560

Cys Thr Thr Val Cys Pro His Ala Gly Lys Ala Lys Ala Glu Lys Val
                        565                 570                 575

Glu Cys Ala Leu Lys Gly Gly Ile Phe Arg Gly Thr Leu Pro Ala Ala
                        580                 585                 590

Asp Cys Pro Gly Ile Asp Thr Thr Val Thr Phe Asn Ala Asp Gly Thr
                        595                 600                 605

Ala Gln Lys Val Glu Leu Ala Leu Glu Lys Lys Ser Ala Pro Ser Pro
                    610                 615                 620

Leu Thr Tyr Arg Gly Thr Trp Met Val Arg Glu Asp Gly Ile Val Glu
        625                 630                 635                 640

Leu Ser Leu Val Ser Ser Glu Gln Ser Lys Ala Pro His Glu Lys Glu
                        645                 650                 655

Leu Tyr Glu Leu Ile Asp Ser Asn Ser Val Arg Tyr Met Gly Ala Pro
                        660                 665                 670

Gly Ala Gly Lys Pro Ser Lys Glu Met Ala Pro Phe Tyr Val Leu Lys
                    675                 680                 685

Lys Thr Lys Lys Leu Ala Thr Lys Ala Val Ser Val Leu Lys Gly Asp
                    690                 695                 700

Gly Pro Val Gln Gly Ile Ile Asn Phe Glu Gln Lys Glu Ser Asn Gly
        705                 710                 715                 720

Pro Val Lys Val Trp Gly Ser Ile Lys Gly Leu Thr Glu Gly Leu His
                        725                 730                 735
```

```
Gly Phe His Val His Glu Phe Gly Asp Asn Thr Ala Gly Cys Thr Ser
            740                 745                 750

Ala Gly Pro His Phe Asn Pro Leu Ser Arg Lys His Gly Pro Lys
        755                 760                 765

Asp Glu Glu Arg His Val Gly Asp Leu Gly Asn Val Thr Ala Asp Lys
770                 775                 780

Asp Gly Val Ala Asp Val Ser Ile Glu Asp Ser Val Ile Ser Leu Ser
785                 790                 795                 800

Gly Asp His Ser Ile Ile Gly Arg Thr Leu Val Val His Glu Lys Ala
            805                 810                 815

Asp Asp Leu Gly Lys Gly Gly Asn Glu Glu Ser Thr Lys Thr Gly Asn
            820                 825                 830

Ala Gly Ser Arg Leu Ala Cys Gly Val Ile Gly Ile Ala Gln
            835                 840                 845

<210> SEQ ID NO 9
<211> LENGTH: 849
<212> TYPE: PRT
<213> ORGANISM: Treponema pallidum
<220> FEATURE:
<221> NAME/KEY: MISC_FEATURE
<222> LOCATION: (5)..(14)
<223> OTHER INFORMATION: 261 tag
<220> FEATURE:
<221> NAME/KEY: MISC_FEATURE
<222> LOCATION: (17)..(150)
<223> OTHER INFORMATION: Treponema pallidum outer membrane protein TP17
<220> FEATURE:
<221> NAME/KEY: MISC_FEATURE
<222> LOCATION: (155)..(277)
<223> OTHER INFORMATION: Treponema pallidum outer membrane protein TP15
<220> FEATURE:
<221> NAME/KEY: MISC_FEATURE
<222> LOCATION: (282)..(695)
<223> OTHER INFORMATION: Treponema pallidum outer membrane protein TP47
<220> FEATURE:
<221> NAME/KEY: MISC_FEATURE
<222> LOCATION: (697)..(849)
<223> OTHER INFORMATION: human copper zinc superoxide dismutase

<400> SEQUENCE: 9

Met Arg Gly Ser Ala Val Pro Pro Gln Gln Trp Ala Leu Ser Gly Ser
1               5                   10                  15

Val Ser Cys Thr Thr Val Cys Pro His Ala Gly Lys Ala Lys Ala Glu
            20                  25                  30

Lys Val Glu Cys Ala Leu Lys Gly Gly Ile Phe Arg Gly Thr Leu Pro
        35                  40                  45

Ala Ala Asp Cys Pro Gly Ile Asp Thr Thr Val Thr Phe Asn Ala Asp
    50                  55                  60

Gly Thr Ala Gln Lys Val Glu Leu Ala Leu Lys Lys Ser Ala Pro
65                  70                  75                  80

Ser Pro Leu Thr Tyr Arg Gly Thr Trp Met Val Arg Glu Asp Gly Ile
                85                  90                  95

Val Glu Leu Ser Leu Val Ser Ser Glu Gln Ser Lys Ala Pro His Glu
            100                 105                 110

Lys Glu Leu Tyr Glu Leu Ile Asp Ser Asn Ser Val Arg Tyr Met Gly
        115                 120                 125

Ala Pro Gly Ala Gly Lys Pro Ser Lys Glu Met Ala Pro Phe Tyr Val
    130                 135                 140

Leu Lys Lys Thr Lys Lys Gly Pro Arg Ser Ser Phe Ser Ile Pro
145                 150                 155                 160
```

```
Asn Gly Thr Tyr Arg Ala Thr Tyr Gln Asp Phe Asp Glu Asn Gly Trp
            165                 170                 175

Lys Asp Phe Leu Glu Val Thr Phe Asp Gly Gly Lys Met Val Gln Val
            180                 185                 190

Val Tyr Asp Tyr Gln His Lys Glu Gly Arg Phe Lys Ser Gln Asp Ala
            195                 200                 205

Asp Tyr His Arg Val Met Tyr Ala Ser Ser Gly Ile Gly Pro Glu Lys
            210                 215                 220

Ala Phe Arg Glu Leu Ala Asp Ala Leu Leu Glu Lys Gly Asn Pro Glu
225                 230                 235                 240

Met Val Asp Val Val Thr Gly Ala Thr Val Ser Ser Gln Ser Phe Arg
            245                 250                 255

Arg Leu Gly Arg Ala Leu Leu Gln Ser Ala Arg Arg Gly Glu Lys Glu
            260                 265                 270

Ala Ile Ile Ser Arg Gly Pro Arg Ser Gly Ser Ser His His Glu Thr
            275                 280                 285

His Tyr Gly Tyr Ala Thr Leu Ser Tyr Ala Asp Tyr Trp Ala Gly Glu
            290                 295                 300

Leu Gly Gln Ser Arg Asp Val Leu Leu Ala Gly Asn Ala Glu Ala Asp
305                 310                 315                 320

Arg Ala Gly Asp Leu Asp Ala Gly Met Phe Asp Ala Val Ser Arg Ala
            325                 330                 335

Thr His Gly His Gly Ala Phe Arg Gln Gln Phe Gln Tyr Ala Val Glu
            340                 345                 350

Val Leu Gly Glu Lys Val Leu Ser Lys Gln Glu Thr Glu Asp Ser Arg
            355                 360                 365

Gly Arg Lys Lys Trp Glu Tyr Glu Thr Asp Pro Ser Val Thr Lys Met
370                 375                 380

Val Arg Ala Ser Ala Ser Phe Gln Asp Leu Gly Glu Asp Gly Glu Ile
385                 390                 395                 400

Lys Phe Glu Ala Val Glu Gly Ala Val Ala Leu Ala Asp Arg Ala Ser
            405                 410                 415

Ser Phe Met Val Asp Ser Glu Glu Tyr Lys Ile Thr Asn Val Lys Val
            420                 425                 430

His Gly Met Lys Phe Val Pro Val Ala Val Pro His Glu Leu Lys Gly
            435                 440                 445

Ile Ala Lys Glu Lys Phe His Phe Val Glu Asp Ser Arg Val Thr Glu
            450                 455                 460

Asn Thr Asn Gly Leu Lys Thr Met Leu Thr Glu Asp Ser Phe Ser Ala
465                 470                 475                 480

Arg Lys Val Ser Ser Met Glu Ser Pro His Asp Leu Val Val Asp Thr
            485                 490                 495

Val Gly Thr Gly Tyr His Ser Arg Phe Gly Ser Asp Ala Glu Ala Ser
            500                 505                 510

Val Met Leu Lys Arg Ala Asp Gly Ser Glu Leu Ser His Arg Glu Phe
            515                 520                 525

Ile Asp Tyr Val Met Asn Phe Asn Thr Val Arg Tyr Asp Tyr Tyr Gly
            530                 535                 540

Asp Asp Ala Ser Tyr Thr Asn Leu Met Ala Ser Tyr Gly Thr Lys His
545                 550                 555                 560

Ser Ala Asp Ser Trp Trp Lys Thr Gly Arg Val Pro Arg Ile Ser Cys
            565                 570                 575
```

```
Gly Ile Asn Tyr Gly Phe Asp Arg Phe Lys Gly Ser Gly Pro Gly Tyr
            580                 585                 590

Tyr Arg Leu Thr Leu Ile Ala Asn Gly Tyr Arg Asp Val Val Ala Asp
        595                 600                 605

Val Arg Phe Leu Pro Lys Tyr Glu Gly Asn Ile Asp Ile Gly Leu Lys
    610                 615                 620

Gly Lys Val Leu Thr Ile Gly Ala Asp Ala Glu Thr Leu Met Asp
625                 630                 635                 640

Ala Ala Val Asp Val Phe Ala Asp Gly Gln Pro Lys Leu Val Ser Asp
                645                 650                 655

Gln Ala Val Ser Leu Gly Gln Asn Val Leu Ser Ala Asp Phe Thr Pro
            660                 665                 670

Gly Thr Glu Tyr Thr Val Glu Val Arg Phe Lys Glu Phe Gly Ser Val
        675                 680                 685

Arg Ala Lys Val Val Ala Gln Leu Ala Thr Lys Ala Val Ser Val Leu
    690                 695                 700

Lys Gly Asp Gly Pro Val Gln Gly Ile Ile Asn Phe Glu Gln Lys Glu
705                 710                 715                 720

Ser Asn Gly Pro Val Lys Val Trp Gly Ser Ile Lys Gly Leu Thr Glu
                725                 730                 735

Gly Leu His Gly Phe His Val His Glu Phe Gly Asp Asn Thr Ala Gly
            740                 745                 750

Cys Thr Ser Ala Gly Pro His Phe Asn Pro Leu Ser Arg Lys His Gly
        755                 760                 765

Gly Pro Lys Asp Glu Glu Arg His Val Gly Asp Leu Gly Asn Val Thr
    770                 775                 780

Ala Asp Lys Asp Gly Val Ala Asp Val Ser Ile Glu Asp Ser Val Ile
785                 790                 795                 800

Ser Leu Ser Gly Asp His Ser Ile Ile Gly Arg Thr Leu Val Val His
                805                 810                 815

Glu Lys Ala Asp Asp Leu Gly Lys Gly Gly Asn Glu Glu Ser Thr Lys
            820                 825                 830

Thr Gly Asn Ala Gly Ser Arg Leu Ala Cys Gly Val Ile Gly Ile Ala
        835                 840                 845

Gln

<210> SEQ ID NO 10
<211> LENGTH: 847
<212> TYPE: PRT
<213> ORGANISM: Treponema pallidum
<220> FEATURE:
<221> NAME/KEY: MISC_FEATURE
<222> LOCATION: (5)..(14)
<223> OTHER INFORMATION: 261 tag
<220> FEATURE:
<221> NAME/KEY: MISC_FEATURE
<222> LOCATION: (17)..(150)
<223> OTHER INFORMATION: Treponema pallidum outer membrane protein TP17
<220> FEATURE:
<221> NAME/KEY: MISC_FEATURE
<222> LOCATION: (155)..(568)
<223> OTHER INFORMATION: Treponema pallidum outer membrane protein TP47
<220> FEATURE:
<221> NAME/KEY: MISC_FEATURE
<222> LOCATION: (571)..(693)
<223> OTHER INFORMATION: Treponema pallidum outer membrane protein TP15
<220> FEATURE:
<221> NAME/KEY: MISC_FEATURE
<222> LOCATION: (695)..(847)
<223> OTHER INFORMATION: human cop

<400> SEQUENCE: 10

```
Met Arg Gly Ser Ala Val Pro Pro Gln Gln Trp Ala Leu Ser Gly Ser
1               5                   10                  15

Val Ser Cys Thr Thr Val Cys Pro His Ala Gly Lys Ala Lys Ala Glu
            20                  25                  30

Lys Val Glu Cys Ala Leu Lys Gly Gly Ile Phe Arg Gly Thr Leu Pro
        35                  40                  45

Ala Ala Asp Cys Pro Gly Ile Asp Thr Thr Val Thr Phe Asn Ala Asp
    50                  55                  60

Gly Thr Ala Gln Lys Val Glu Leu Ala Leu Glu Lys Lys Ser Ala Pro
65                  70                  75                  80

Ser Pro Leu Thr Tyr Arg Gly Thr Trp Met Val Arg Glu Asp Gly Ile
                85                  90                  95

Val Glu Leu Ser Leu Val Ser Ser Glu Gln Ser Lys Ala Pro His Glu
            100                 105                 110

Lys Glu Leu Tyr Glu Leu Ile Asp Ser Asn Ser Val Arg Tyr Met Gly
        115                 120                 125

Ala Pro Gly Ala Gly Lys Pro Ser Lys Glu Met Ala Pro Phe Tyr Val
    130                 135                 140

Leu Lys Lys Thr Lys Lys Gly Pro Arg Ser Gly Ser His His Glu
145                 150                 155                 160

Thr His Tyr Gly Tyr Ala Thr Leu Ser Tyr Ala Asp Tyr Trp Ala Gly
                165                 170                 175

Glu Leu Gly Gln Ser Arg Asp Val Leu Leu Ala Gly Asn Ala Glu Ala
            180                 185                 190

Asp Arg Ala Gly Asp Leu Asp Ala Gly Met Phe Asp Ala Val Ser Arg
        195                 200                 205

Ala Thr His Gly His Gly Ala Phe Arg Gln Gln Phe Gln Tyr Ala Val
    210                 215                 220

Glu Val Leu Gly Glu Lys Val Leu Ser Lys Gln Glu Thr Glu Asp Ser
225                 230                 235                 240

Arg Gly Arg Lys Lys Trp Glu Tyr Glu Thr Asp Pro Ser Val Thr Lys
                245                 250                 255

Met Val Arg Ala Ser Ala Ser Phe Gln Asp Leu Gly Glu Asp Gly Glu
            260                 265                 270

Ile Lys Phe Glu Ala Val Glu Gly Ala Val Ala Leu Ala Asp Arg Ala
        275                 280                 285

Ser Ser Phe Met Val Asp Ser Glu Glu Tyr Lys Ile Thr Asn Val Lys
    290                 295                 300

Val His Gly Met Lys Phe Val Pro Val Ala Val Pro His Glu Leu Lys
305                 310                 315                 320

Gly Ile Ala Lys Glu Lys Phe His Phe Val Glu Asp Ser Arg Val Thr
                325                 330                 335

Glu Asn Thr Asn Gly Leu Lys Thr Met Leu Thr Glu Asp Ser Phe Ser
            340                 345                 350

Ala Arg Lys Val Ser Ser Met Glu Ser Pro His Asp Leu Val Val Asp
        355                 360                 365

Thr Val Gly Thr Gly Tyr His Ser Arg Phe Gly Ser Asp Ala Glu Ala
    370                 375                 380

Ser Val Met Leu Lys Arg Ala Asp Gly Ser Glu Leu Ser His Arg Glu
385                 390                 395                 400

Phe Ile Asp Tyr Val Met Asn Phe Asn Thr Val Arg Tyr Asp Tyr Tyr
                405                 410                 415
```

```
Gly Asp Asp Ala Ser Tyr Thr Asn Leu Met Ala Ser Tyr Gly Thr Lys
            420                 425                 430

His Ser Ala Asp Ser Trp Trp Lys Thr Gly Arg Val Pro Arg Ile Ser
            435                 440                 445

Cys Gly Ile Asn Tyr Gly Phe Asp Arg Phe Lys Gly Ser Gly Pro Gly
            450                 455                 460

Tyr Tyr Arg Leu Thr Leu Ile Ala Asn Gly Tyr Arg Asp Val Val Ala
465                 470                 475                 480

Asp Val Arg Phe Leu Pro Lys Tyr Glu Gly Asn Ile Asp Ile Gly Leu
            485                 490                 495

Lys Gly Lys Val Leu Thr Ile Gly Gly Ala Asp Ala Glu Thr Leu Met
            500                 505                 510

Asp Ala Ala Val Asp Val Phe Ala Asp Gly Gln Pro Lys Leu Val Ser
            515                 520                 525

Asp Gln Ala Val Ser Leu Gly Gln Asn Val Leu Ser Ala Asp Phe Thr
            530                 535                 540

Pro Gly Thr Glu Tyr Thr Val Glu Val Arg Phe Lys Glu Phe Gly Ser
545                 550                 555                 560

Val Arg Ala Lys Val Ala Gln Gly Pro Ser Phe Ser Ser Ile Pro
            565                 570                 575

Asn Gly Thr Tyr Arg Ala Thr Tyr Gln Asp Phe Asp Glu Asn Gly Trp
            580                 585                 590

Lys Asp Phe Leu Glu Val Thr Phe Asp Gly Gly Lys Met Val Gln Val
            595                 600                 605

Val Tyr Asp Tyr Gln His Lys Glu Gly Arg Phe Lys Ser Gln Asp Ala
            610                 615                 620

Asp Tyr His Arg Val Met Tyr Ala Ser Ser Gly Ile Gly Pro Glu Lys
625                 630                 635                 640

Ala Phe Arg Glu Leu Ala Asp Ala Leu Leu Glu Lys Gly Asn Pro Glu
            645                 650                 655

Met Val Asp Val Val Thr Gly Ala Thr Val Ser Ser Gln Ser Phe Arg
            660                 665                 670

Arg Leu Gly Arg Ala Leu Leu Gln Ser Ala Arg Arg Gly Glu Lys Glu
            675                 680                 685

Ala Ile Ile Ser Arg Leu Ala Thr Lys Ala Val Ser Val Leu Lys Gly
            690                 695                 700

Asp Gly Pro Val Gln Gly Ile Ile Asn Phe Glu Gln Lys Glu Ser Asn
705                 710                 715                 720

Gly Pro Val Lys Val Trp Gly Ser Ile Lys Gly Leu Thr Glu Gly Leu
            725                 730                 735

His Gly Phe His Val His Glu Phe Gly Asp Asn Thr Ala Gly Cys Thr
            740                 745                 750

Ser Ala Gly Pro His Phe Asn Pro Leu Ser Arg Lys His Gly Gly Pro
            755                 760                 765

Lys Asp Glu Glu Arg His Val Gly Asp Leu Gly Asn Val Thr Ala Asp
            770                 775                 780

Lys Asp Gly Val Ala Asp Val Ser Ile Glu Asp Ser Val Ile Ser Leu
785                 790                 795                 800

Ser Gly Asp His Ser Ile Ile Gly Arg Thr Leu Val Val His Glu Lys
            805                 810                 815

Ala Asp Asp Leu Gly Lys Gly Gly Asn Glu Glu Ser Thr Lys Thr Gly
            820                 825                 830
```

```
Asn Ala Gly Ser Arg Leu Ala Cys Gly Val Ile Gly Ile Ala Gln
        835                 840                 845
```

```
<210> SEQ ID NO 11
<211> LENGTH: 847
<212> TYPE: PRT
<213> ORGANISM: Treponema pallidum
<220> FEATURE:
<221> NAME/KEY: MISC_FEATURE
<222> LOCATION: (5)..(14)
<223> OTHER INFORMATION: 261 tag
<220> FEATURE:
<221> NAME/KEY: MISC_FEATURE
<222> LOCATION: (17)..(430)
<223> OTHER INFORMATION: Treponema pallidum outer membrane protein TP47
<220> FEATURE:
<221> NAME/KEY: MISC_FEATURE
<222> LOCATION: (435)..(557)
<223> OTHER INFORMATION: Treponema pallidum outer membrane protein TP15
<220> FEATURE:
<221> NAME/KEY: MISC_FEATURE
<222> LOCATION: (560)..(693)
<223> OTHER INFORMATION: Treponema pallidum outer membrane protein TP17
<220> FEATURE:
<221> NAME/KEY: MISC_FEATURE
<222> LOCATION: (695)..(847)
<223> OTHER INFORMATION: human copper zinc superoxide dismutase

<400> SEQUENCE: 11

Met Arg Gly Ser Ala Val Pro Pro Gln Gln Trp Ala Leu Ser Gly Ser
1               5                   10                  15

Gly Ser Ser His His Glu Thr His Tyr Gly Tyr Ala Thr Leu Ser Tyr
            20                  25                  30

Ala Asp Tyr Trp Ala Gly Glu Leu Gly Gln Ser Arg Asp Val Leu Leu
        35                  40                  45

Ala Gly Asn Ala Glu Ala Asp Arg Ala Gly Asp Leu Asp Ala Gly Met
    50                  55                  60

Phe Asp Ala Val Ser Arg Ala Thr His Gly His Gly Ala Phe Arg Gln
65                  70                  75                  80

Gln Phe Gln Tyr Ala Val Glu Val Leu Gly Glu Lys Val Leu Ser Lys
                85                  90                  95

Gln Glu Thr Glu Asp Ser Arg Gly Arg Lys Lys Trp Glu Tyr Glu Thr
            100                 105                 110

Asp Pro Ser Val Thr Lys Met Val Arg Ala Ser Ala Ser Phe Gln Asp
        115                 120                 125

Leu Gly Glu Asp Gly Glu Ile Lys Phe Glu Ala Val Glu Gly Ala Val
130                 135                 140

Ala Leu Ala Asp Arg Ala Ser Ser Phe Met Val Asp Ser Glu Glu Tyr
145                 150                 155                 160

Lys Ile Thr Asn Val Lys Val His Gly Met Lys Phe Val Pro Val Ala
                165                 170                 175

Val Pro His Glu Leu Lys Gly Ile Ala Lys Glu Lys Phe His Phe Val
            180                 185                 190

Glu Asp Ser Arg Val Thr Glu Asn Thr Asn Gly Leu Lys Thr Met Leu
        195                 200                 205

Thr Glu Asp Ser Phe Ser Ala Arg Lys Val Ser Ser Met Glu Ser Pro
210                 215                 220

His Asp Leu Val Val Asp Thr Val Gly Thr Gly Tyr His Ser Arg Phe
225                 230                 235                 240

Gly Ser Asp Ala Glu Ala Ser Val Met Leu Lys Arg Ala Asp Gly Ser
                245                 250                 255
```

```
Glu Leu Ser His Arg Glu Phe Ile Asp Tyr Val Met Asn Phe Asn Thr
                260                 265                 270

Val Arg Tyr Asp Tyr Tyr Gly Asp Asp Ala Ser Tyr Thr Asn Leu Met
            275                 280                 285

Ala Ser Tyr Gly Thr Lys His Ser Ala Asp Ser Trp Trp Lys Thr Gly
        290                 295                 300

Arg Val Pro Arg Ile Ser Cys Gly Ile Asn Tyr Gly Phe Asp Arg Phe
305                 310                 315                 320

Lys Gly Ser Gly Pro Gly Tyr Tyr Arg Leu Thr Leu Ile Ala Asn Gly
                325                 330                 335

Tyr Arg Asp Val Val Ala Asp Val Arg Phe Leu Pro Lys Tyr Glu Gly
            340                 345                 350

Asn Ile Asp Ile Gly Leu Lys Gly Lys Val Leu Thr Ile Gly Gly Ala
        355                 360                 365

Asp Ala Glu Thr Leu Met Asp Ala Val Asp Val Phe Ala Asp Gly
        370                 375                 380

Gln Pro Lys Leu Val Ser Asp Gln Ala Val Ser Leu Gly Gln Asn Val
385                 390                 395                 400

Leu Ser Ala Asp Phe Thr Pro Gly Thr Glu Tyr Thr Val Glu Val Arg
                405                 410                 415

Phe Lys Glu Phe Gly Ser Val Arg Ala Lys Val Val Ala Gln Gly Pro
            420                 425                 430

Arg Ser Ser Phe Ser Ser Ile Pro Asn Gly Thr Tyr Arg Ala Thr Tyr
        435                 440                 445

Gln Asp Phe Asp Glu Asn Gly Trp Lys Asp Phe Leu Glu Val Thr Phe
450                 455                 460

Asp Gly Gly Lys Met Val Gln Val Val Tyr Asp Tyr Gln His Lys Glu
465                 470                 475                 480

Gly Arg Phe Lys Ser Gln Asp Ala Asp Tyr His Arg Val Met Tyr Ala
                485                 490                 495

Ser Ser Gly Ile Gly Pro Glu Lys Ala Phe Arg Glu Leu Ala Asp Ala
            500                 505                 510

Leu Leu Glu Lys Gly Asn Pro Glu Met Val Asp Val Val Thr Gly Ala
        515                 520                 525

Thr Val Ser Ser Gln Ser Phe Arg Arg Leu Gly Arg Ala Leu Leu Gln
        530                 535                 540

Ser Ala Arg Arg Gly Glu Lys Glu Ala Ile Ile Ser Arg Gly Pro Val
545                 550                 555                 560

Ser Cys Thr Thr Val Cys Pro His Ala Gly Lys Ala Lys Ala Glu Lys
                565                 570                 575

Val Glu Cys Ala Leu Lys Gly Gly Ile Phe Arg Gly Thr Leu Pro Ala
            580                 585                 590

Ala Asp Cys Pro Gly Ile Asp Thr Thr Val Thr Phe Asn Ala Asp Gly
        595                 600                 605

Thr Ala Gln Lys Val Glu Leu Ala Leu Glu Lys Ser Ala Pro Ser
        610                 615                 620

Pro Leu Thr Tyr Arg Gly Thr Trp Met Val Arg Glu Asp Gly Ile Val
625                 630                 635                 640

Glu Leu Ser Leu Val Ser Ser Glu Gln Ser Lys Ala Pro His Glu Lys
                645                 650                 655

Glu Leu Tyr Glu Leu Ile Asp Ser Asn Ser Val Arg Tyr Met Gly Ala
            660                 665                 670

Pro Gly Ala Gly Lys Pro Ser Lys Glu Met Ala Pro Phe Tyr Val Leu
```

```
            675                 680                 685
Lys Lys Thr Lys Lys Leu Ala Thr Lys Ala Val Ser Val Leu Lys Gly
            690                 695                 700

Asp Gly Pro Val Gln Gly Ile Ile Asn Phe Glu Gln Lys Glu Ser Asn
705                 710                 715                 720

Gly Pro Val Lys Val Trp Gly Ser Ile Lys Gly Leu Thr Glu Gly Leu
                725                 730                 735

His Gly Phe His Val His Glu Phe Gly Asp Asn Thr Ala Gly Cys Thr
            740                 745                 750

Ser Ala Gly Pro His Phe Asn Pro Leu Ser Arg Lys His Gly Gly Pro
            755                 760                 765

Lys Asp Glu Glu Arg His Val Gly Asp Leu Gly Asn Val Thr Ala Asp
770                 775                 780

Lys Asp Gly Val Ala Asp Val Ser Ile Glu Asp Ser Val Ile Ser Leu
785                 790                 795                 800

Ser Gly Asp His Ser Ile Ile Gly Arg Thr Leu Val Val His Glu Lys
                805                 810                 815

Ala Asp Asp Leu Gly Lys Gly Gly Asn Glu Glu Ser Thr Lys Thr Gly
            820                 825                 830

Asn Ala Gly Ser Arg Leu Ala Cys Gly Val Ile Gly Ile Ala Gln
            835                 840                 845

<210> SEQ ID NO 12
<211> LENGTH: 849
<212> TYPE: PRT
<213> ORGANISM: Treponema pallidum
<220> FEATURE:
<221> NAME/KEY: MISC_FEATURE
<222> LOCATION: (5)..(14)
<223> OTHER INFORMATION: 261 tag
<220> FEATURE:
<221> NAME/KEY: MISC_FEATURE
<222> LOCATION: (17)..(430)
<223> OTHER INFORMATION: Treponema pallidum outer membrane protein TP47
<220> FEATURE:
<221> NAME/KEY: MISC_FEATURE
<222> LOCATION: (435)..(568)
<223> OTHER INFORMATION: Treponema pallidum outer membrane protein TP17
<220> FEATURE:
<221> NAME/KEY: MISC_FEATURE
<222> LOCATION: (573)..(695)
<223> OTHER INFORMATION: Treponema pallidum outer membrane protein TP15
<220> FEATURE:
<221> NAME/KEY: MISC_FEATURE
<222> LOCATION: (697)..(849)
<223> OTHER INFORMATION: human copper zinc superoxide dismutase

<400> SEQUENCE: 12

Met Arg Gly Ser Ala Val Pro Pro Gln Gln Trp Ala Leu Ser Gly Ser
1               5                   10                  15

Gly Ser Ser His His Glu Thr His Tyr Gly Tyr Ala Thr Leu Ser Tyr
            20                  25                  30

Ala Asp Tyr Trp Ala Gly Glu Leu Gly Gln Ser Arg Asp Val Leu Leu
        35                  40                  45

Ala Gly Asn Ala Glu Ala Asp Arg Ala Gly Asp Leu Asp Ala Gly Met
    50                  55                  60

Phe Asp Ala Val Ser Arg Ala Thr His Gly His Gly Ala Phe Arg Gln
65                  70                  75                  80

Gln Phe Gln Tyr Ala Val Glu Val Leu Gly Glu Lys Val Leu Ser Lys
                85                  90                  95

Gln Glu Thr Glu Asp Ser Arg Gly Arg Lys Lys Trp Glu Tyr Glu Thr
```

```
            100                 105                 110
Asp Pro Ser Val Thr Lys Met Val Arg Ala Ser Ala Ser Phe Gln Asp
            115                 120                 125

Leu Gly Glu Asp Gly Glu Ile Lys Phe Glu Ala Val Glu Gly Ala Val
        130                 135                 140

Ala Leu Ala Asp Arg Ala Ser Ser Phe Met Val Asp Ser Glu Glu Tyr
145                 150                 155                 160

Lys Ile Thr Asn Val Lys Val His Gly Met Lys Phe Val Pro Val Ala
                165                 170                 175

Val Pro His Glu Leu Lys Gly Ile Ala Lys Glu Lys Phe His Phe Val
            180                 185                 190

Glu Asp Ser Arg Val Thr Glu Asn Thr Asn Gly Leu Lys Thr Met Leu
        195                 200                 205

Thr Glu Asp Ser Phe Ser Ala Arg Lys Val Ser Met Glu Ser Pro
210                 215                 220

His Asp Leu Val Val Asp Thr Val Gly Thr Gly Tyr His Ser Arg Phe
225                 230                 235                 240

Gly Ser Asp Ala Glu Ala Ser Val Met Leu Lys Arg Ala Asp Gly Ser
                245                 250                 255

Glu Leu Ser His Arg Glu Phe Ile Asp Tyr Val Met Asn Phe Asn Thr
            260                 265                 270

Val Arg Tyr Asp Tyr Tyr Gly Asp Asp Ala Ser Tyr Thr Asn Leu Met
        275                 280                 285

Ala Ser Tyr Gly Thr Lys His Ser Ala Asp Ser Trp Trp Lys Thr Gly
290                 295                 300

Arg Val Pro Arg Ile Ser Cys Gly Ile Asn Tyr Gly Phe Asp Arg Phe
305                 310                 315                 320

Lys Gly Ser Gly Pro Gly Tyr Tyr Arg Leu Thr Leu Ile Ala Asn Gly
                325                 330                 335

Tyr Arg Asp Val Val Ala Asp Val Arg Phe Leu Pro Lys Tyr Glu Gly
            340                 345                 350

Asn Ile Asp Ile Gly Leu Lys Gly Lys Val Leu Thr Ile Gly Gly Ala
        355                 360                 365

Asp Ala Glu Thr Leu Met Asp Ala Ala Val Asp Val Phe Ala Asp Gly
370                 375                 380

Gln Pro Lys Leu Val Ser Asp Gln Ala Val Ser Leu Gly Gln Asn Val
385                 390                 395                 400

Leu Ser Ala Asp Phe Thr Pro Gly Thr Glu Tyr Thr Val Glu Val Arg
                405                 410                 415

Phe Lys Glu Phe Gly Ser Val Arg Ala Lys Val Val Ala Gln Gly Pro
            420                 425                 430

Arg Ser Val Ser Cys Thr Thr Val Cys Pro His Ala Gly Lys Ala Lys
        435                 440                 445

Ala Glu Lys Val Glu Cys Ala Leu Lys Gly Gly Ile Phe Arg Gly Thr
450                 455                 460

Leu Pro Ala Ala Asp Cys Pro Gly Ile Asp Thr Thr Val Thr Phe Asn
465                 470                 475                 480

Ala Asp Gly Thr Ala Gln Lys Val Glu Leu Ala Leu Glu Lys Lys Ser
                485                 490                 495

Ala Pro Ser Pro Leu Thr Tyr Arg Gly Thr Trp Met Val Arg Glu Asp
            500                 505                 510

Gly Ile Val Glu Leu Ser Leu Val Ser Ser Glu Gln Ser Lys Ala Pro
        515                 520                 525
```

His Glu Lys Glu Leu Tyr Glu Leu Ile Asp Ser Asn Ser Val Arg Tyr
         530                 535                 540

Met Gly Ala Pro Gly Ala Gly Lys Pro Ser Lys Glu Met Ala Pro Phe
545                 550                 555                 560

Tyr Val Leu Lys Lys Thr Lys Leu Gly Pro Arg Ser Ser Phe Ser Ser
                565                 570                 575

Ile Pro Asn Gly Thr Tyr Arg Ala Thr Tyr Gln Asp Phe Asp Glu Asn
            580                 585                 590

Gly Trp Lys Asp Phe Leu Glu Val Thr Phe Asp Gly Lys Met Val
        595                 600                 605

Gln Val Val Tyr Asp Tyr Gln His Lys Glu Gly Arg Phe Lys Ser Gln
    610                 615                 620

Asp Ala Asp Tyr His Arg Val Met Tyr Ala Ser Ser Gly Ile Gly Pro
625                 630                 635                 640

Glu Lys Ala Phe Arg Glu Leu Ala Asp Ala Leu Leu Glu Lys Gly Asn
                645                 650                 655

Pro Glu Met Val Asp Val Val Thr Gly Ala Thr Val Ser Ser Gln Ser
            660                 665                 670

Phe Arg Arg Leu Gly Arg Ala Leu Leu Gln Ser Ala Arg Arg Gly Glu
675                 680                 685

Lys Glu Ala Ile Ile Ser Arg Leu Ala Thr Lys Ala Val Ser Val Leu
    690                 695                 700

Lys Gly Asp Gly Pro Val Gln Gly Ile Ile Asn Phe Glu Gln Lys Glu
705                 710                 715                 720

Ser Asn Gly Pro Val Lys Val Trp Gly Ser Ile Lys Gly Leu Thr Glu
                725                 730                 735

Gly Leu His Gly Phe His Val His Glu Phe Gly Asp Asn Thr Ala Gly
            740                 745                 750

Cys Thr Ser Ala Gly Pro His Phe Asn Pro Leu Ser Arg Lys His Gly
        755                 760                 765

Gly Pro Lys Asp Glu Glu Arg His Val Gly Asp Leu Gly Asn Val Thr
    770                 775                 780

Ala Asp Lys Asp Gly Val Ala Asp Val Ser Ile Glu Asp Ser Val Ile
785                 790                 795                 800

Ser Leu Ser Gly Asp His Ser Ile Ile Gly Arg Thr Leu Val Val His
                805                 810                 815

Glu Lys Ala Asp Asp Leu Gly Lys Gly Gly Asn Glu Glu Ser Thr Lys
            820                 825                 830

Thr Gly Asn Ala Gly Ser Arg Leu Ala Cys Gly Val Ile Gly Ile Ala
        835                 840                 845

Gln

<210> SEQ ID NO 13
<211> LENGTH: 30
<212> TYPE: DNA
<213> ORGANISM: Artificial Sequence
<220> FEATURE:
<223> OTHER INFORMATION: Primer

<400> SEQUENCE: 13
cacagaattc attaaagagg agaaattaac                                          30

<210> SEQ ID NO 14
<211> LENGTH: 30
<212> TYPE: DNA

```
<213> ORGANISM: Artificial Sequence
<220> FEATURE:
<223> OTHER INFORMATION: Primer

<400> SEQUENCE: 14
tgtctgggcc cagcttttct agtattccga                                      30

<210> SEQ ID NO 15
<211> LENGTH: 28
<212> TYPE: DNA
<213> ORGANISM: Artificial Sequence
<220> FEATURE:
<223> OTHER INFORMATION: Primer

<400> SEQUENCE: 15
tgtctgggcc cgtgagctgc accacggt                                        28

<210> SEQ ID NO 16
<211> LENGTH: 38
<212> TYPE: DNA
<213> ORGANISM: Artificial Sequence
<220> FEATURE:
<223> OTHER INFORMATION: Primer

<400> SEQUENCE: 16
agctggagat ctcgggccgc gagagataat ggcttctt                             38

<210> SEQ ID NO 17
<211> LENGTH: 34
<212> TYPE: DNA
<213> ORGANISM: Artificial Sequence
<220> FEATURE:
<223> OTHER INFORMATION: Primer

<400> SEQUENCE: 17
gctggagatc taccgcgaga gataatggct tctt                                 34

<210> SEQ ID NO 18
<211> LENGTH: 42
<212> TYPE: DNA
<213> ORGANISM: Artificial Sequence
<220> FEATURE:
<223> OTHER INFORMATION: Primer

<400> SEQUENCE: 18
agctggagat ctcgggcctt tcttggtttt cttcagaacg ta                        42

<210> SEQ ID NO 19
<211> LENGTH: 37
<212> TYPE: DNA
<213> ORGANISM: Artificial Sequence
<220> FEATURE:
<223> OTHER INFORMATION: Primer

<400> SEQUENCE: 19
agctggagat cttggaccct gcgccaccac tttcgcg                              37

<210> SEQ ID NO 20
<211> LENGTH: 25
<212> TYPE: DNA
<213> ORGANISM: Artificial Sequence
<220> FEATURE:
<223> OTHER INFORMATION: Primer

<400> SEQUENCE: 20
cgcgaccgtg agctctcaga gtttt                                           25
```

<210> SEQ ID NO 21
<211> LENGTH: 54
<212> TYPE: DNA
<213> ORGANISM: Artificial Sequence
<220> FEATURE:
<223> OTHER INFORMATION: Primer

<400> SEQUENCE: 21
cagcacgctg acggctttgg tcgcgaggcg agagataatg gcttctttt cgcc        54

<210> SEQ ID NO 22
<211> LENGTH: 17
<212> TYPE: DNA
<213> ORGANISM: Artificial Sequence
<220> FEATURE:
<223> OTHER INFORMATION: Primer

<400> SEQUENCE: 22
gtgagctgca ccacggt                                                  17

<210> SEQ ID NO 23
<211> LENGTH: 53
<212> TYPE: DNA
<213> ORGANISM: Artificial Sequence
<220> FEATURE:
<223> OTHER INFORMATION: Primer

<400> SEQUENCE: 23
cagcacgctg acggctttgg tcgcgagttt cttggttttc ttcagaacgt aaa          53

<210> SEQ ID NO 24
<211> LENGTH: 18
<212> TYPE: DNA
<213> ORGANISM: Artificial Sequence
<220> FEATURE:
<223> OTHER INFORMATION: Primer

<400> SEQUENCE: 24
ggttagcgat caggccgt                                                 18

<210> SEQ ID NO 25
<211> LENGTH: 49
<212> TYPE: DNA
<213> ORGANISM: Artificial Sequence
<220> FEATURE:
<223> OTHER INFORMATION: Primer

<400> SEQUENCE: 25
cagcacgctg acggctttgg tcgcgagctg cgccaccact ttcgcgcgc               49

<210> SEQ ID NO 26
<211> LENGTH: 54
<212> TYPE: DNA
<213> ORGANISM: Artificial Sequence
<220> FEATURE:
<223> OTHER INFORMATION: Primer

<400> SEQUENCE: 26
ggcgaaaaag aagccattat ctctcgcctc gcgaccaaag ccgtcagcgt gctg         54

<210> SEQ ID NO 27
<211> LENGTH: 53
<212> TYPE: DNA
<213> ORGANISM: Artificial Sequence
<220> FEATURE:

```
<223> OTHER INFORMATION: Primer

<400> SEQUENCE: 27
tttacgttct gaagaaaacc aagaaactcg cgaccaaagc cgtcagcgtg ctg         53

<210> SEQ ID NO 28
<211> LENGTH: 49
<212> TYPE: DNA
<213> ORGANISM: Artificial Sequence
<220> FEATURE:
<223> OTHER INFORMATION: Primer

<400> SEQUENCE: 28
gcgcgcgaaa gtggtggcgc agctcgcgac caaagccgtc agcgtgctg              49

<210> SEQ ID NO 29
<211> LENGTH: 21
<212> TYPE: DNA
<213> ORGANISM: Artificial Sequence
<220> FEATURE:
<223> OTHER INFORMATION: Primer

<400> SEQUENCE: 29
tgcagtcgac gggcccggga t                                            21

<210> SEQ ID NO 30
<211> LENGTH: 25
<212> TYPE: DNA
<213> ORGANISM: Artificial Sequence
<220> FEATURE:
<223> OTHER INFORMATION: Primer

<400> SEQUENCE: 30
cgcgaccgtg agctctcaga gtttt                                        25

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
ccctgccggc cgcagattgt                                              20

<210> SEQ ID NO 32
<211> LENGTH: 26
<212> TYPE: DNA
<213> ORGANISM: Artificial Sequence
<220> FEATURE:
<223> OTHER INFORMATION: Primer

<400> SEQUENCE: 32
ggatttcacc ccgggtaccg aatata                                       26

<210> SEQ ID NO 33
<211> LENGTH: 37
<212> TYPE: DNA
<213> ORGANISM: Artificial Sequence
<220> FEATURE:
<223> OTHER INFORMATION: Primer

<400> SEQUENCE: 33
agccaagctt cattactggg cgataccaat aacgcca                           37
```